(12) United States Patent
Kumar et al.

(10) Patent No.: US 12,203,085 B2
(45) Date of Patent: Jan. 21, 2025

(54) 3'UTR SEQUENCE FOR TRANSGENE EXPRESSION

(71) Applicant: Corteva Agriscience LLC, Indianapolis, IN (US)

(72) Inventors: Sandeep Kumar, Johnston, IA (US); Sara Bennett, Indianapolis, IN (US); Andrew J. Bowling, Indianapolis, IN (US); Alicia Walker, Indianapolis, IN (US); Cory M. Larsen, Zionsville, IN (US); Heather Pence, Indianapolis, IN (US); Staci Weaver, Indianapolis, IN (US); Ronnie Hampton, Jr., Indianapolis, IN (US)

(73) Assignee: CORTEVA AGRISCIENCE, LLC, IN (US)

( * ) Notice: Subject to any disclaimer, the term of this patent is extended or adjusted under 35 U.S.C. 154(b) by 483 days.

(21) Appl. No.: 17/551,455

(22) Filed: Dec. 15, 2021

(65) Prior Publication Data
US 2022/0098606 A1    Mar. 31, 2022

Related U.S. Application Data

(63) Continuation of application No. 16/139,112, filed on Sep. 24, 2018, now Pat. No. 11,236,350.

(60) Provisional application No. 62/567,836, filed on Oct. 4, 2017.

(51) Int. Cl.
  C12N 15/82    (2006.01)
  A01H 6/60     (2018.01)

(52) U.S. Cl.
  CPC ......... *C12N 15/8233* (2013.01); *A01H 6/604* (2018.05)

(58) Field of Classification Search
  None
  See application file for complete search history.

(56) References Cited

U.S. PATENT DOCUMENTS

| | | |
|---|---|---|
| 11,236,350 B2 | 2/2022 | Kumar et al. |
| 2004/0168217 A1 | 8/2004 | Lowe et al. |
| 2013/0180009 A1 | 7/2013 | Albertsen et al. |
| 2015/0247157 A1 | 9/2015 | Chamberlin et al. |

OTHER PUBLICATIONS

Ortega et al., The 3' untranslated region of a soybean cytosolic glutamine synthetase (GS1) affects transcript stability and protein accumulation in transgenic alfalfa, 2006, The Plant Journal, vol. 45(5), pp. 832-846. (Year: 2006).*

Cho H-T., et al., "Regulation of Root hair Initiation and Expansin Gene Expression in *Arabidopsis*," Plant Cell, Dec. 2002, vol. 14, pp. 3237-3253.

Emrich S.J., et al., "Nearly Identical Paralogs: Implications for Maize (*Zea mays* L.) Genome Evolution," Genetics, Jan. 2007, vol. 175, No. 1, pp. 429-439.

Harikrishnan S.L., et al., "Sequence and Gene Expression Evolution of Paralogous Genes in Willows," Scientific reports, Dec. 22, 2015, vol. 5, Article No. 18662, 10 Pages.

Hernandez-Garcia C.M., et al., "A Soybean (*Glycine max*) Polyubiquitin Promoter Gives Strong Constitutive Expression in Transgenic Soybean," Plant Cell Reports, 2009, vol. 28, pp. 837-849.

Kim Y., et al., "A 20 Nucleotide Upstream Element is Essential for the Nopaline Synthase (nos) Promoter Activity," Plant Molecular Biology, 1994, vol. 24, pp. 105-117.

Awit S.J., et al., "Transgenic Manipulation of Plant Embryo Sacs Tracked Through Cell-type-specific Fluorescent Markers: Cell labeling, Cell ablation, and Adventitious Embryos," Plant Reproduction, 2013, vol. 26, pp. 125-137.

NCBI Genbank: "Predicted: Glycine Max Egg Cell-Secreted Protein 1.3-like (LOC102667984), mRNA," NCBI Reference Sequence: XM_006588234.2, Published Nov. 25, 2015, 1 Page.

Piechulla B., et al., "Identification of Tomato Lhc Promoter Regions Necessary for Circadian Expression," Plant Molecular Biology, 1998, vol. 38, pp. 655-662.

Resentini F., "The Female Gametophyte: Development and Functions," PHD Thesis, Universita Degli Studi Di Milano, 2012-2013, pp. 1, 23, Retrieved from URL: https://air.unimi.it/handle/2434/228141#.YBqyq_2pXAww.

Rombauts S., et al., "PlantCARE, a Plant Cis-acting Regulatory Element Database," Nucleic Acids Research, 1999, vol. 27, No. 1, pp. 295-296.

Ross E.J.H., et al., "Activation of the Oryza Sativa Non-Symbiotic Haemoglobin-2 Promoter by the Cytokinin-Regulated Transcription Factor, ARR1," Journal of Experimental Botany, Aug. 2004, vol. 55, No. 403, pp. 1721-1731.

Singh V.K., et al., "Genome-Wide Survey and Comprehensive Expression Profiling of Aux/IAA Gene Family in Chickpea and Soybean," Frontiers in Plant Science, Oct. 2015, vol. 6, Article. 918, 15 Pages.

Wang J., et al., "Divergent Evolutionary and Expression Patterns Between Lineage Specific New Duplicate Genes and their Parental Paralogs in *Arabidopsis thaliana*," PLoS One, Aug. 29, 2013, vol. 8, No. 8(e72362), 11 Pages.

Wang Z-P., et al., "Egg Cell-Specific Promoter Controlled CRISPR/Cas9 Efficiently Generates Homozygous Mutants for Multiple Target Genes in *Arabidopsis* in a Single Generation, " Genome Biology, 2015, vol. 16, No. 144, 12 Pages.

(Continued)

*Primary Examiner* — Cathy Kingdon
*Assistant Examiner* — Christina L Meadows

(57) ABSTRACT

This disclosure concerns compositions and methods for promoting transcription of a nucleotide sequence in a plant or plant cell, employing a promoter from a *Glycine max* egg cell gene. Some embodiments relate to a promoter or a 5' UTR from a *Glycine max* egg cell gene that functions in plants to promote transcription of operably linked nucleotide sequences. Other embodiments relate to a 3' UTR or a terminator from a *Glycine max* egg cell gene that functions in plants to promote transcription of operably linked nucleotide sequences.

9 Claims, No Drawings

Specification includes a Sequence Listing.

(56) References Cited

OTHER PUBLICATIONS

Welsch R., et al., "Structural and Functional Characterization of the Phytoene Synthase Promoter from Arabidopsis Thaliana," 2003, Planta, vol. 216, pp. 523-534.

* cited by examiner

3'UTR SEQUENCE FOR TRANSGENE EXPRESSION

INCORPORATION BY REFERENCE OF MATERIAL SUBMITTED ELECTRONICALLY

This application claims the benefit of U.S. Provisional Patent Application Ser. No. 62/567,836 filed Oct. 4, 2017, which is expressly incorporated by reference in its entirety herein.

Incorporated by reference in its entirety is a computer-readable nucleotide/amino acid sequence listing submitted concurrently herewith and identified as follows: one 12.7 KB ASCII (Text) file named "80788-US-NP 20170931 Sequence_ST25" created on Oct. 2, 2017.

BACKGROUND

Many plant species are capable of being transformed with transgenes to introduce agronomically desirable traits or characteristics. The resulting plant species are developed and/or modified to have particular desirable traits. Generally, desirable traits include, for example, improving nutritional value quality, increasing yield, conferring pest or disease resistance, increasing drought and stress tolerance, improving horticultural qualities (e.g., pigmentation and growth), imparting herbicide tolerance, enabling the production of industrially useful compounds and/or materials from the plant, and/or enabling the production of pharmaceuticals.

Transgenic plant species comprising multiple transgenes stacked at a single genomic locus are produced via plant transformation technologies. Plant transformation technologies result in the introduction of a transgene into a plant cell, recovery of a fertile transgenic plant that contains the stably integrated copy of the transgene in the plant genome, and subsequent transgene expression via transcription and translation results in transgenic plants that possess desirable traits and phenotypes. However, novel gene regulatory elements that allow the production of transgenic plant species to highly express multiple transgenes engineered as a trait stack are desirable.

Likewise, novel gene regulatory elements that allow the expression of a transgene within particular tissues or organs of a plant are desirable. For example, increased resistance of a plant to infection by soil-borne pathogens might be accomplished by transforming the plant genome with a pathogen-resistance gene such that pathogen-resistance protein is robustly expressed within the roots of the plant. Alternatively, it may be desirable to express a transgene in plant tissues that are in a particular growth or developmental phase such as, for example, cell division or elongation. Furthermore, it may be desirable to express a transgene in leaf and stem tissues of a plant to provide tolerance against herbicides, or resistance against above ground insects and pests.

Therefore, a need exists for new gene regulatory elements that can drive the desired levels of expression of transgenes in specific plant tissues.

BRIEF SUMMARY

In embodiments of the subject disclosure, the disclosure relates to a nucleic acid vector comprising a promoter operably linked to: a polylinker sequence; a non-*Glycine max* egg cell heterologous coding sequence; wherein said promoter comprises a polynucleotide sequence that has at least 95% sequence identity with SEQ ID NO:2. In further embodiments, said promoter is 1,089 bp in length. In other embodiments, said promoter consists of a polynucleotide sequence that has at least 95% sequence identity with SEQ ID NO:2. In additional embodiments, said promoter is operably linked to a heterologous coding sequence. Accordingly, the heterologous coding sequence encodes a selectable marker protein, an insecticidal resistance protein, a herbicide tolerance protein, a nitrogen use efficiency protein, a water use efficiency protein, a small RNA molecule, a nutritional quality protein, or a DNA binding protein. In other embodiments, the nucleic acid vector comprises a terminator polynucleotide sequence. In additional embodiments, the nucleic acid vector comprises a 3' untranslated polynucleotide sequence. In additional embodiments, the nucleic acid vector comprises a 5' untranslated polynucleotide sequence. In additional embodiments, the nucleic acid vector comprises an intron sequence. In additional embodiments, said promoter has ovule preferred tissue expression. In further embodiments, the nucleic acid vector comprises a polynucleotide sequence that has at least 95% sequence identity with SEQ ID NO:2 operably linked to a heterologous coding sequence. In further embodiments, said plant is selected from the group consisting of *Zea mays*, wheat, rice, sorghum, oats, rye, bananas, sugar cane, *Glycine max*, cotton, *Arabidopsis*, tobacco, sunflower, and canola. In yet another embedment, said plant is *Glycine max*. In some embodiments, the heterologous coding sequence is inserted into the genome of said plant. In other embodiments, the promoter comprises a polynucleotide sequence having at least 95% sequence identity with SEQ ID NO:2 and said promoter is operably linked to a heterologous coding sequence. In additional embodiments, the transgenic plant comprises a 3' untranslated sequence. In further embodiments, said heterologous coding sequence has ovule preferred tissue expression. In additional embodiments, the transgenic plant comprises said promoter of 1,089 bp in length.

In embodiments of the subject disclosure, the disclosure relates to a method for producing a transgenic plant cell, the method comprising the steps of transforming a plant cell with a gene expression cassette comprising a *Glycine max* egg cell promoter operably linked to at least one polynucleotide sequence of interest; isolating the transformed plant cell comprising the gene expression cassette; and, producing a transgenic plant cell comprising the *Glycine max* egg cell promoter operably linked to at least one polynucleotide sequence of interest. In other embodiments, the transformation of a plant cell is performed with a plant transformation method. In some aspects, the plant transformation method is selected from the group consisting of an *Agrobacterium*-mediated transformation method, a biolistics transformation method, a silicon carbide transformation method, a protoplast transformation method, and a liposome transformation method. In further embodiments, the polynucleotide sequence of interest is expressed in a plant cell. In other embodiments, the polynucleotide sequence of interest is stably integrated into the genome of the transgenic plant cell. In further embodiments, the method comprises regenerating the transgenic plant cell into a transgenic plant; and, obtaining the transgenic plant, wherein the transgenic plant comprising the gene expression cassette comprising the *Glycine max* egg cell promoter of operably linked to at least one polynucleotide sequence of interest. In other embodiments, the transgenic plant cell is a monocotyledonous transgenic plant cell or a dicotyledonous transgenic plant cell. Examples of a dicotyledonous transgenic plant cell includes an *Arabidopsis* plant cell, a tobacco plant cell, a *Glycine max* plant cell, a canola plant cell, and a cotton plant cell. Examples of a monocotyledonous transgenic plant cell includes a Zea mays plant cell, a rice plant cell, and a wheat plant cell. In some embodiments, the *Glycine max* egg cell promoter comprises the polynucleotide of SEQ ID NO:2. In other embodiments, the *Glycine max* egg cell promoter comprises a first polynucleotide sequence of interest operably linked to the 3' end of SEQ ID NO:2. In additional embodiments, the method comprises introducing into the plant cell a polynucleotide sequence of interest operably linked to a *Glycine max* egg cell promoter. In further embodiments, the polynucleotide sequence of interest operably linked to the *Glycine max* egg cell promoter is introduced into the plant cell by a plant transformation method. Examples of plant transformation methods include *Agrobacterium*-mediated transformation method, a biolistics transformation method, a silicon carbide transformation method, a protoplast transformation method, and a liposome transformation method. In further embodiments, the polynucleotide sequence of interest is expressed in ovule cell tissue. In additional embodiments, the polynucleotide sequence of interest is stably integrated into the genome of the plant cell. In some embodiments, the transgenic plant cell is a monocotyledonous plant cell or a dicotyledonous plant cell. Examples of dicotyledonous plant cells include an *Arabidopsis* plant cell, a tobacco plant cell, a *Glycine max* plant cell, a canola plant cell, and a cotton plant cell. Examples of monocotyledonous plant cells include a *Zea mays* plant cell, a rice plant cell, and a wheat plant cell.

In embodiments of the subject disclosure, the disclosure relates to a transgenic plant cell comprising a *Glycine max* egg cell promoter. In other embodiments, the transgenic plant cell comprises a transgenic event. In further embodiments, the transgenic event comprises an agronomic trait. Examples of agronomic traits include an insecticidal resistance trait, herbicide tolerance trait, nitrogen use efficiency trait, water use efficiency trait, nutritional quality trait, DNA binding trait, selectable marker trait, small RNA trait, or any combination thereof. In further embodiments, the agronomic trait comprises an herbicide tolerant trait. In an aspect of this embodiment, the herbicide tolerant trait comprises an aad-1 coding sequence. In yet another embodiment, the transgenic plant cell produces a commodity product. Examples of a commodity product includes protein concentrate, protein isolate, grain, meal, flour, oil, or fiber. In further embodiments, the transgenic plant cell is selected from the group consisting of a dicotyledonous plant cell or a monocotyledonous plant cell. For example, the dicotyledonous plant cell is a *Glycine max* plant cell. In additional embodiments, the *Glycine max* egg cell promoter comprises a polynucleotide with at least 95% sequence identity to the polynucleotide of SEQ ID NO:2. In other embodiments, the *Glycine max* egg cell promoter is 1,089 bp in length. In some embodiments, the *Glycine max* egg cell promoter consists of SEQ ID NO:2. In subsequent embodiments, the *Glycine max* egg cell promoter comprises a first polynucleotide sequence of interest operably linked to the 3' end of SEQ ID NO:2. In other embodiments, the agronomic trait is expressed in plant tissues. In further embodiments, the isolated polynucleotide comprises a nucleic acid sequence with at least 95% sequence identity to the polynucleotide of SEQ ID NO:2. In additional embodiments, the isolated polynucleotide drives ovule preferred tissue expression. In other embodiments, the isolated polynucleotide comprises expression activity within a plant cell. In some embodiments, the isolated polynucleotide comprise an open-reading frame polynucleotide coding for a polypeptide; and a termination sequence. In subsequent embodiments, the polynucleotide of SEQ ID NO:2 is 1,089 bp in length.

In embodiments of the subject disclosure, the disclosure relates to a gene expression cassette comprising a promoter operably linked to a heterologous coding sequence, wherein the promoter comprises a polynucleotide comprising a sequence identity of at least 95% to SEQ ID NO:2. In some embodiments, the polynucleotide has at least 95% sequence identity to SEQ ID NO:2. In additional embodiments, the gene expression cassette comprises an intron. In further embodiments, the gene expression cassette comprises a 5' UTR. In subsequent embodiments, the promoter has ovule preferred tissue expression. In other embodiments, the promoter is operably linked to a heterologous coding sequence that encodes a polypeptide or a small RNA gene. Examples of the encoded polypeptide or small RNA gene include a heterologous coding sequence conferring insecticidal resistance, herbicide tolerance, a nucleic acid conferring nitrogen use efficiency, a nucleic acid conferring water use efficiency, a nucleic acid conferring nutritional quality, a nucleic acid encoding a DNA binding protein, and a nucleic acid encoding a selectable marker. In additional embodiments, the gene expression cassette comprises a 3' untranslated region. For example, the 3' untranslated region has at least 95% sequence identity to SEQ ID NO:3. In additional embodiments, the gene expression cassette comprises a 5' untranslated region. In additional embodiments, the gene expression cassette comprises a terminator region. For example, the terminator region has at least 95% sequence identity to SEQ ID NO:3. In other embodiments the subject disclosure relates to a recombinant vector comprising the gene expression cassette, wherein the vector is selected from the group consisting of a plasmid, a cosmid, a bacterial artificial chromosome, a virus, and a bacteriophage. In other embodiments the subject disclosure relates to a transgenic cell comprising the gene expression cassette. In an aspect of this embodiment, the transgenic cell is a transgenic plant cell. In other aspects of this embodiment the transgenic plant comprises the transgenic plant cell. In further aspects the transgenic plant is a monocotyledonous plant or dicotyledonous plant. Examples of a monocotyledonous plant is include a maize plant, a rice plant, and a wheat plant. In further aspects of the embodiment, the transgenic plant produces a seed comprising the gene expression cassette. In other embodiments, the promoter is an ovule preferred tissue promoter. In some embodiments, the promoter is a constitutive promoter.

The foregoing and other features will become more apparent from the following detailed description of several embodiments, which proceeds with reference to the accompanying FIGURES.

DETAILED DESCRIPTION

I. Overview of Several Embodiments

Development of transgenic plant products is becoming increasingly complex. Commercially viable transgenic plants now require the stacking of multiple transgenes into a single locus. Plant promoters and 3' UTRs/terminators used for basic research or biotechnological applications are generally unidirectional, directing only one gene that has been fused at its 3' end (downstream) for the promoter, or at its 5' end (upstream) for the 3' UTR/terminator. Accordingly, each transgene/heterologous coding sequence usually requires a promoter and 3' UTR/terminator for expression, wherein multiple regulatory elements are required to express multiple transgenes within one gene stack. With an increasing number of transgenes in gene stacks, the same promoter and/or 3' UTR/terminator is routinely used to obtain optimal levels of expression patterns of different transgenes. Obtaining optimal levels of transgene/heterologous coding sequence expression is necessary for the production of a single polygenic trait. Unfortunately, multi-gene constructs driven by the same promoter and/or 3' UTR/terminator are known to cause gene silencing resulting in less efficacious transgenic products in the field. The repeated promoter and/or 3' UTR/terminator elements may lead to homology-based gene silencing. In addition, repetitive sequences within a transgene/heterologous coding sequence may lead to gene intra locus homologous recombination resulting in polynucleotide rearrangements. The silencing and rearrangement of transgenes will likely have an undesirable affect on the performance of a transgenic plant produced to express transgenes. Further, excess of transcription factor (TF)-binding sites due to promoter repetition can cause depletion of endogenous TFs leading to transcriptional inactivation. Given the need to introduce multiple genes into plants for metabolic engineering and trait stacking, a variety of promoters and/or 3' UTRs/terminators are required to develop transgenic crops that drive the expression of multiple genes.

A particular problem in promoter and/or 3' UTR/terminator identification is the need to identify tissue-specific/preferred promoters, related to specific cell types, developmental stages and/or functions in the plant that are not expressed in other plant tissues. Tissue specific (i.e., tissue preferred) or organ specific promoters drive gene expression in a certain tissue such as in the kernel, root, leaf, or tapetum of the plant. Tissue and developmental stage specific promoters and/or 3' UTRs/terminators can be initially identified from observing the expression of genes, which are expressed in particular tissues or at particular time periods during plant development. These tissue specific/preferred promoters and/or 3' UTRs/terminators are required for certain applications in the transgenic plant industry and are desirable as they permit specific expression of heterologous genes in a tissue and/or developmental stage selective manner, indicating expression of the heterologous gene differentially at various organs, tissues and/or times, but not in other undesirable tissues. For example, increased resistance of a plant to infection by soil-borne pathogens might be accomplished by transforming the plant genome with a pathogen-resistance gene such that pathogen-resistance protein is robustly expressed within the roots of the plant. Alternatively, it may be desirable to express a transgene/heterologous coding sequence in plant tissues that are in a particular growth or developmental phase such as, for example, cell division or elongation. Another application is the desirability of using tissue specific/preferred promoters and/or 3' UTRs/terminators to confine the expression of the transgenes encoding an agronomic trait in specific tissues types like developing parenchyma cells. As such, a particular problem in the identification of promoters and/or 3' UTRs/terminators is how to identify the promoters, and to relate the identified promoter to developmental properties of the cell for specific/preferred tissue expression.

Another problem regarding the identification of a promoter is the requirement to clone all relevant cis-acting and trans-activating transcriptional control elements so that the cloned DNA fragment drives transcription in the wanted specific expression pattern. Given that such control elements are located distally from the translation initiation or start site, the size of the polynucleotide that is selected to comprise the promoter is of importance for providing the level of expression and the expression patterns of the promoter polynucleotide sequence. It is known that promoter lengths include functional information, and different genes have been shown to have promoters longer or shorter than promoters of the other genes in the genome. Elucidating the transcription start site of a promoter and predicting the functional gene elements in the promoter region is challenging. Further adding to the challenge are the complexity, diversity and inherent degenerate nature of regulatory motifs and cis- and trans-regulatory elements (Blanchette, Mathieu, et al. "Genome-wide computational prediction of transcriptional regulatory modules reveals new insights into human gene expression." Genome research 16.5 (2006): 656-668). The cis- and trans-regulatory elements are located in the distal parts of the promoter which regulate the spatial and temporal expression of a gene to occur only at required sites and at specific times (Porto, Milena Silva, et al. "Plant promoters: an approach of structure and function." Molecular biotechnology 56.1 (2014): 38-49). Accordingly, the identification of promoter regulatory elements requires that an appropriate sequence of a specific size containing the necessary cis- and trans-regulatory elements is obtained that will result in driving expression of an operably linked transgene/heterologous coding sequence in a desirable manner.

Provided are methods and compositions for overcoming such problems through the use of *Glycine max* egg cell gene regulatory elements to express transgenes in planta.

II. Terms and Abbreviations

Throughout the application, a number of terms are used. In order to provide a clear and consistent understanding of the specification and claims, including the scope to be given such terms, the following definitions are provided.

As used herein, the articles, "a," "an," and "the" include plural references unless the context clearly and unambiguously dictates otherwise.

The term "isolated", as used herein means having been removed from its natural environment, or removed from other compounds present when the compound is first formed. The term "isolated" embraces materials isolated from natural sources as well as materials (e.g., nucleic acids and proteins) recovered after preparation by recombinant expression in a host cell, or chemically-synthesized compounds such as nucleic acid molecules, proteins, and peptides.

The term "purified", as used herein relates to the isolation of a molecule or compound in a form that is substantially free of contaminants normally associated with the molecule or compound in a native or natural environment, or substantially enriched in concentration relative to other compounds present when the compound is first formed, and means having been increased in purity as a result of being separated from other components of the original composition. The term "purified nucleic acid" is used herein to describe a nucleic acid sequence which has been separated, produced apart from, or purified away from other biological compounds including, but not limited to polypeptides, lipids and carbohydrates, while effecting a chemical or functional change in the component (e.g., a nucleic acid may be purified from a chromosome by removing protein contaminants and breaking chemical bonds connecting the nucleic acid to the remaining DNA in the chromosome).

The term "synthetic", as used herein refers to a polynucleotide (i.e., a DNA or RNA) molecule that was created via chemical synthesis as an in vitro process. For example, a synthetic DNA may be created during a reaction within an Eppendorf™ tube, such that the synthetic DNA is enzymatically produced from a native strand of DNA or RNA. Other laboratory methods may be utilized to synthesize a polynucleotide sequence. Oligonucleotides may be chemically synthesized on an oligo synthesizer via solid-phase synthesis using phosphoramidites. The synthesized oligonucleotides may be annealed to one another as a complex, thereby producing a "synthetic" polynucleotide. Other methods for chemically synthesizing a polynucleotide are known in the art, and can be readily implemented for use in the present disclosure.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

For the purposes of the present disclosure, a "gene," includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, introns and locus control regions.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

As used herein a "transgene" is defined to be a nucleic acid sequence that encodes a gene product, including for example, but not limited to, an mRNA. In one embodiment the transgene/heterologous coding sequence is an exogenous nucleic acid, where the transgene/heterologous coding sequence has been introduced into a host cell by genetic engineering (or the progeny thereof) where the transgene/heterologous coding sequence is not normally found. In one example, a transgene/heterologous coding sequence encodes an industrially or pharmaceutically useful compound, or a gene encoding a desirable agricultural trait (e.g., an herbicide-resistance gene). In yet another example, a transgene/heterologous coding sequence is an antisense nucleic acid sequence, wherein expression of the antisense nucleic acid sequence inhibits expression of a target nucleic acid sequence. In one embodiment the transgene/heterologous coding sequence is an endogenous nucleic acid, wherein additional genomic copies of the endogenous nucleic acid are desired, or a nucleic acid that is in the antisense orientation with respect to the sequence of a target nucleic acid in a host organism.

As used herein the term "non-*Glycine max* egg cell transgene" or "non-*Glycine max* egg cell gene" is any transgene/heterologous coding sequence that has less than 80% sequence identity with the *Glycine max* egg cell gene coding sequence (SEQ ID NO:4 with the Genbank NCBI Accession No. GM09G195200).

As used herein, "heterologous DNA coding sequence" means any coding sequence other than the one that naturally encodes the *Glycine max* egg cell gene, or any homolog of the expressed *Glycine max* egg cell protein. The term "heterologous" is used in the context of this invention for any combination of nucleic acid sequences that is not normally found intimately associated in nature.

A "gene product" as defined herein is any product produced by the gene. For example the gene product can be the direct transcriptional product of a gene (e.g., mRNA, tRNA, rRNA, antisense RNA, interfering RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation. Gene expression can be influenced by external signals, for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein the term "gene expression" relates to the process by which the coded information of a nucleic acid transcriptional unit (including, e.g., genomic DNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein, "homology-based gene silencing" (HBGS) is a generic term that includes both transcriptional gene silencing and post-transcriptional gene silencing. Silencing of a target locus by an unlinked silencing locus can result from transcription inhibition (transcriptional gene silencing; TGS) or mRNA degradation (post-transcriptional gene silencing; PTGS), owing to the production of double-stranded RNA (dsRNA) corresponding to promoter or transcribed sequences, respectively. The involvement of distinct cellular components in each process suggests that dsRNA-induced TGS and PTGS likely result from the diversification of an ancient common mechanism. However, a strict comparison of TGS and PTGS has been difficult to achieve because it generally relies on the analysis of distinct silencing loci. In some instances, a single transgene locus can triggers both TGS and PTGS, owing to the production of dsRNA corresponding to promoter and transcribed sequences of different target genes. Mourrain et al. (2007)

*Planta* 225:365-79. It is likely that siRNAs are the actual molecules that trigger TGS and PTGS on homologous sequences: the siRNAs would in this model trigger silencing and methylation of homologous sequences in cis and in trans through the spreading of methylation of transgene sequences into the endogenous promoter.

As used herein, the term "nucleic acid molecule" (or "nucleic acid" or "polynucleotide") may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide". A nucleic acid molecule is usually at least 10 bases in length, unless otherwise specified. The term may refer to a molecule of RNA or DNA of indeterminate length. The term includes single- and double-stranded forms of DNA. A nucleic acid molecule may include either or both naturally-occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidites, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

Transcription proceeds in a 5' to 3' manner along a DNA strand. This means that RNA is made by the sequential addition of ribonucleotide-5'-triphosphates to the 3' terminus of the growing chain (with a requisite elimination of the pyrophosphate). In either a linear or circular nucleic acid molecule, discrete elements (e.g., particular nucleotide sequences) may be referred to as being "upstream" or "5'" relative to a further element if they are bonded or would be bonded to the same nucleic acid in the 5' direction from that element. Similarly, discrete elements may be "downstream" or "3'" relative to a further element if they are or would be bonded to the same nucleic acid in the 3' direction from that element.

A base "position", as used herein, refers to the location of a given base or nucleotide residue within a designated nucleic acid. The designated nucleic acid may be defined by alignment (see below) with a reference nucleic acid.

Hybridization relates to the binding of two polynucleotide strands via Hydrogen bonds. Oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide and the DNA or RNA target. The oligonucleotide need not be 100% complementary to its target sequence to be specifically hybridizable. An oligonucleotide is specifically hybridizable when binding of the oligonucleotide to the target DNA or RNA molecule interferes with the normal function of the target DNA or RNA, and there is sufficient degree of complementarity to avoid non-specific binding of the oligonucleotide to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the chosen hybridization method and the composition and length of the hybridizing nucleic acid sequences. Generally, the temperature of hybridization and the ionic strength (especially the Na+ and/or Mg2+ concentration) of the hybridization buffer will contribute to the stringency of hybridization, though wash times also influence stringency. Calculations regarding hybridization conditions required for attaining particular degrees of stringency are discussed in Sambrook et al. (ed.), *Molecular Cloning: A Laboratory Manual,* 2nd ed., vol. 1-3, Cold Spring Harbor Laboratory Press, Cold Spring Harbor, New York, 1989, chs. 9 and 11.

As used herein, "stringent conditions" encompass conditions under which hybridization will only occur if there is less than 50% mismatch between the hybridization molecule and the DNA target. "Stringent conditions" include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize.

In particular embodiments, stringent conditions can include hybridization at 65° C., followed by washes at 65° C. with 0.1×SSC/0.1% SDS for 40 minutes.

The following are representative, non-limiting hybridization conditions:

Very High Stringency: Hybridization in 5×SSC buffer at 65° C. for 16 hours; wash twice in 2×SSC buffer at room temperature for 15 minutes each; and wash twice in 0.5×SSC buffer at 65° C. for 20 minutes each.

High Stringency: Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Moderate Stringency: Hybridization in 6×SSC buffer at room temperature to 55° C. for 16-20 hours; wash at least twice in 2×-3×SSC buffer at room temperature to 55° C. for 20-30 minutes each.

In particular embodiments, specifically hybridizable nucleic acid molecules can remain bound under very high stringency hybridization conditions. In these and further embodiments, specifically hybridizable nucleic acid molecules can remain bound under high stringency hybridization conditions. In these and further embodiments, specifically hybridizable nucleic acid molecules can remain bound under moderate stringency hybridization conditions.

As used herein, the term "oligonucleotide" refers to a short nucleic acid polymer. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of small DNA sequences. In PCR, the oligonucleotide is typically referred to as a "primer", which allows a DNA polymerase to extend the oligonucleotide and replicate the complementary strand.

The terms "percent sequence identity" or "percent identity" or "identity" are used interchangeably to refer to a sequence comparison based on identical matches between correspondingly identical positions in the sequences being compared between two or more amino acid or nucleotide sequences. The percent identity refers to the extent to which two optimally aligned polynucleotide or peptide sequences are invariant throughout a window of alignment of components, e.g., nucleotides or amino acids. Hybridization experiments and mathematical algorithms known in the art may be used to determine percent identity. Many mathematical algorithms exist as sequence alignment computer programs known in the art that calculate percent identity. These programs may be categorized as either global sequence alignment programs or local sequence alignment programs.

Global sequence alignment programs calculate the percent identity of two sequences by comparing alignments end-to-end in order to find exact matches, dividing the number of exact matches by the length of the shorter sequences, and then multiplying by 100. Basically, the percentage of identical nucleotides in a linear polynucleotide sequence of a reference ("query) polynucleotide molecule as compared to a test ("subject") polynucleotide molecule when the two sequences are optimally aligned (with appropriate nucleotide insertions, deletions, or gaps).

Local sequence alignment programs are similar in their calculation, but only compare aligned fragments of the sequences rather than utilizing an end-to-end analysis. Local sequence alignment programs such as BLAST can be used to compare specific regions of two sequences. A BLAST comparison of two sequences results in an E-value, or expectation value, that represents the number of different alignments with scores equivalent to or better than the raw alignment score, S, that are expected to occur in a database search by chance. The lower the E value, the more significant the match. Because database size is an element in E-value calculations, E-values obtained by BLASTing against public databases, such as GENBANK, have generally increased over time for any given query/entry match. In setting criteria for confidence of polypeptide function prediction, a "high" BLAST match is considered herein as having an E-value for the top BLAST hit of less than 1E-30; a medium BLASTX E-value is 1E-30 to 1E-8; and a low BLASTX E-value is greater than 1E-8. The protein function assignment in the present invention is determined using combinations of E-values, percent identity, query coverage and hit coverage. Query coverage refers to the percent of the query sequence that is represented in the BLAST alignment. Hit coverage refers to the percent of the database entry that is represented in the BLAST alignment. In one embodiment of the invention, function of a query polypeptide is inferred from function of a conserved protein sequence where either (1) hit_p<1e-30 or % identity >35% AND query_coverage>50% AND hit_coverage>50%, or (2) hit_p<1e-8 AND query_coverage>70% AND hit_coverage>70%. The following abbreviations are produced during a BLAST analysis of a sequence.

| | |
|---|---|
| SEQ_NUM | provides the SEQ ID NO for the listed recombinant polynucleotide sequences. |
| CONTIG_ID | provides an arbitrary sequence name taken from the name of the clone from which the cDNA sequence was obtained. |
| PROTEIN_NUM | provides the SEQ ID NO for the recombinant polypeptide sequence |
| NCBI_GI | provides the GenBank ID number for the top BLAST hit for the sequence. The top BLAST hit is indicated by the National Center for Biotechnology Information GenBank Identifier number. |
| NCBI_GI_DESCRIPTION | refers to the description of the GenBank top BLAST hit for the sequence. |
| E_VALUE | provides the expectation value for the top BLAST match. |
| MATCH_LENGTH | provides the length of the sequence which is aligned in the top BLAST matche |
| TOP_HIT_PCT_IDENT | refers to the percentage of identically matched nucleotides (or residues) that exist along the length of that portion of the sequences which is aligned in the top BLAST match. |
| CAT_TYPE | indicates the classification scheme used to classify the sequence. GO_BP = Gene Ontology Consortium - biological process; GO_CC = Gene Ontology Consortium - cellular component; GO_MF = Gene Ontology Consortium - molecular function; KEGG = KEGG functional hierarchy (KEGG = Kyoto Encyclopedia of Genes and Genomes); EC = Enzyme Classification from ENZYME data bank release 25.0; POI = Pathways of Interest. |
| CAT_DESC | provides the classification scheme subcategory to which the query sequence was assigned. |
| PRODUCT_CAT_DESC | provides the FunCAT annotation category to which the query sequence was assigned. |
| PRODUCT_HIT_DESC | provides the description of the BLAST hit which resulted in assignment of the sequence to the function category provided in the cat_desc column. |
| HIT_E | provides the E value for the BLAST hit in the hit_desc column. |
| PCT_IDENT | refers to the percentage of identically matched nucleotides (or residues) that exist along the length of that portion of the sequences which is aligned in the BLAST match provided in hit_desc. |
| QRY_RANGE | lists the range of the query sequence aligned with the hit. |
| HIT_RANGE | lists the range of the hit sequence aligned with the query. |
| QRY_CVRG | provides the percent of query sequence length that matches to the hit (NCBI). sequence in the BLAST match (% qry cvrg = (match length/query total length) × 100). |
| HIT_CVRG | provides the percent of hit sequence length that matches to the query sequence in the match generated using BLAST (% hit cvrg = (match length/hit total length) × 100). |

Methods for aligning sequences for comparison are well-known in the art. Various programs and alignment algorithms are described. In an embodiment, the subject disclosure relates to calculating percent identity between two polynucleotides or amino acid sequences using an AlignX alignment program of the Vector NTI suite (Invitrogen, Carlsbad, CA). The AlignX alignment program is a global sequence alignment program for polynucleotides or proteins. In an embodiment, the subject disclosure relates to calculating percent identity between two polynucleotides or amino acid sequences using the MegAlign program of the LASERGENE bioinformatics computing suite (MegAlign™ ©1993-2016). DNASTAR. Madison, WI). The MegAlign program is global sequence alignment program for polynucleotides or proteins. In an embodiment, the subject disclosure relates to calculating percent identity between two polynucleotides or amino acid sequences using the Clustal suite of alignment programs, including, but not limited to, ClustalW and ClustalV (Higgins and Sharp (1988) Gene. December 15; 73(1):237-44; Higgins and Sharp (1989) *CABIOS* 5:151-3; Higgins et al. (1992) *Comput. Appl. Biosci.* 8:189-91). In an embodiment, the subject disclosure relates to calculating percent identity between two polynucleotides or amino acid sequences using the GCG suite of programs (Wisconsin Package Version 9.0, Genetics Computer Group (GCG), Madison, WI). In an embodiment, the subject disclosure relates to calculating percent identity between two polynucleotides or amino acid sequences using the BLAST suite of alignment programs, for example, but not limited to, BLASTP, BLASTN, BLASTX, etc. (Altschul et al. (1990) *J. Mol. Biol.* 215:403-10). Further examples of such BLAST alignment programs include Gapped-BLAST or PSI-BLAST (Altschul et al., 1997). In an embodiment, the subject disclosure relates to calculating percent identity between two polynucleotides or amino acid sequences using the FASTA suite of alignment programs, including, but not limited to, FASTA, TFASTX, TFASTY, SSEARCH, LALIGN etc. (Pearson (1994) Comput. Methods Genome Res. [Proc. Int. Symp.], Meeting Date 1992 (Suhai and Sandor, Eds.), Plenum: New York, NY, pp. 111-20). In an embodiment, the subject disclosure relates to calculating percent identity between two polynucleotides or amino acid sequences using the T-Coffee alignment program (Notredame, et. al. (2000) *J. Mol. Biol.* 302, 205-17). In an embodiment, the subject disclosure relates to calculating percent identity between two polynucleotides or amino acid sequences using the DIALIGN suite of alignment programs, including, but not limited to DIALIGN, CHAOS, DIALIGN-TX, DIALIGN-T etc. (Al Ait, et. al. (2013) DIALIGN at GOBICS Nuc. *Acids Research* 41, W3-W7). In an embodiment, the subject disclosure relates to calculating percent identity between two polynucleotides or amino acid sequences using the MUSCLE suite of alignment programs (Edgar (2004) *Nucleic Acids Res.* 32(5): 1792-1797). In an embodiment, the subject disclosure relates to calculating percent identity between two polynucleotides or amino acid sequences using the MAFFT alignment program (Katoh, et. al. (2002) *Nucleic Acids Research* 30(14): 3059-3066). In an embodiment, the subject disclosure relates to calculating percent identity between two polynucleotides or amino acid sequences using the Genoogle program (Albrecht, Felipe. arXiv150702987v1 [cs.DC] 10 Jul. 2015). In an embodiment, the subject disclosure relates to calculating percent identity between two polynucleotides or amino acid sequences using the HMMER suite of programs (Eddy. (1998) *Bioinformatics*, 14:755-63). In an embodiment, the subject disclosure relates to calculating percent identity between two polynucleotides or amino acid sequences using the PLAST suite of alignment programs, including, but not limited to, TPLASTN, PLASTP, KLAST, and PLASTX (Nguyen & Lavenier. (2009) *BMC Bioinformatics*, 10:329). In an embodiment, the subject disclosure relates to calculating percent identity between two polynucleotides or amino acid sequences using the USEARCH alignment program (Edgar (2010) *Bioinformatics* 26(19), 2460-61). In an embodiment, the subject disclosure relates to calculating percent identity between two polynucleotides or amino acid sequences using the SAM suite of alignment programs (Hughey & Krogh (January 1995) *Technical Report UCSCOCRL*-95-7, University of California, Santa Cruz). In an embodiment, the subject disclosure relates to calculating percent identity between two polynucleotides or amino acid sequences using the IDF Searcher (O'Kane, K. C., The Effect of Inverse Document Frequency Weights on Indexed Sequence Retrieval, *Online Journal of Bioinformatics*, Volume 6 (2) 162-173, 2005). In an embodiment, the subject disclosure relates to calculating percent identity between two polynucleotides or amino acid sequences using the Parasail alignment program. (Daily, Jeff. Parasail: SIMD C library for global, semi-global, and local pairwise sequence alignments. *BMC Bioinformatics.* 17:18. Feb. 10, 2016). In an embodiment, the subject disclosure relates to calculating percent identity between two polynucleotides or amino acid sequences using the ScalaBLAST alignment program (Oehmen C, Nieplocha J. "ScalaBLAST: A scalable implementation of BLAST for high-performance data-intensive bioinformatics analysis." *IEEE Transactions on Parallel & Distributed Systems* 17 (8): 740-749 August 2006). In an embodiment, the subject disclosure relates to calculating percent identity between two polynucleotides or amino acid sequences using the SWIPE alignment program (Rognes, T. Faster Smilth-Waterman database searches with inter-sequence SIMD parallelization. *BMC Bioinformatics.* 12, 221 (2011)). In an embodiment, the subject disclosure relates to calculating percent identity between two polynucleotides or amino acid sequences using the ACANA alignment program (Weichun Huang, David M. Umbach, and Leping Li, Accurate anchoring alignment of divergent sequences. Bioinformatics 22:29-34, Jan. 1 2006). In an embodiment, the subject disclosure relates to calculating percent identity between two polynucleotides or amino acid sequences using the DOTLET alignment program (Junier, T. & Pagni, M. DOTLET: diagonal plots in a web browser. Bioinformatics 16(2): 178-9 Feb. 2000). In an embodiment, the subject disclosure relates to calculating percent identity between two polynucleotides or amino acid sequences using the G-PAS alignment program (Frohmberg, W., et al. G-PAS 2.0—an improved version of protein alignment tool with an efficient backtracking routine on multiple GPUs. *Bulletin of the Polish Academy of Sciences Technical Sciences*, Vol. 60, 491 November 2012). In an embodiment, the subject disclosure relates to calculating percent identity between two polynucleotides or amino acid sequences using the GapMis alignment program (Flouri, T. et. al., *Gap Mis: A tool for pairwise sequence alignment with a single gap. Recent Pat DNA Gene Seq.* 7(2): 84-95 August 2013). In an embodiment, the subject disclosure relates to calculating percent identity between two polynucleotides or amino acid sequences using the EMBOSS suite of alignment programs, including, but not limited to: Matcher, Needle, Stretcher, Water, Wordmatch, etc. (Rice, P., Longden, I. & Bleasby, A. EMBOSS: The European Molecular Biology Open Software Suite. *Trends in Genetics* 16(6) 276-77 (2000)). In an embodiment, the subject disclosure relates to calculating percent identity between two polynucleotides or amino acid sequences using the Ngila alignment program (Cartwright, R. Ngila: global pairwise alignments with logarithmic and affine gap costs. Bioinformatics. 23(11): 1427-28. Jun. 1, 2007). In an embodiment, the subject disclosure relates to calculating percent identity between two polynucleotides or amino acid sequences using the probA, also known as propA, alignment program (Miickstein, U., Hofacker, IL, & Stadler, PF. Stochastic pairwise alignments. *Bioinformatics*

18 Suppl. 2:S153-60. 2002). In an embodiment, the subject disclosure relates to calculating percent identity between two polynucleotides or amino acid sequences using the SEQALN suite of alignment programs (Hardy, P. & Waterman, M. *The Sequence Alignment Software Library at USC.* 1997). In an embodiment, the subject disclosure relates to calculating percent identity between two polynucleotides or amino acid sequences using the SIM suite of alignment programs, including, but not limited to, GAP, NAP, LAP, etc. (Huang, X & Miller, W. A Time-Efficient, Linear-Space Local Similarity Algorithm. *Advances in Applied Mathematics*, vol. 12 (1991) 337-57). In an embodiment, the subject disclosure relates to calculating percent identity between two polynucleotides or amino acid sequences using the UGENE alignment program (Okonechnikov, K., Golosova, O. & Fursov, M. Unipro UGENE: a unified bioinformatics toolkit. *Bioinformatics.* 2012 28:1166-67). In an embodiment, the subject disclosure relates to calculating percent identity between two polynucleotides or amino acid sequences using the BAli-Phy alignment program (Suchard, MA & Redelings, BD. BAli-Phy: simultaneous Bayesian inference of alignment and phylogeny. *Bioinformatics.* 22:2047-48. 2006). In an embodiment, the subject disclosure relates to calculating percent identity between two polynucleotides or amino acid sequences using the Base-By-Base alignment program (Brodie, R., et. al. Base-By-Base: Single nucleotide-level analysis of whole viral genome alignments, *BMC Bioinformatics,* 5, 96, 2004). In an embodiment, the subject disclosure relates to calculating percent identity between two polynucleotides or amino acid sequences using the DECIPHER alignment program (ES Wright (2015) "DECIPHER: harnessing local sequence context to improve protein multiple sequence alignment." *BMC Bioinformatics*, doi:10.1186/s12859-015-0749-z.). In an embodiment, the subject disclosure relates to calculating percent identity between two polynucleotides or amino acid sequences using the FSA alignment program (Bradley, R K, et. al. (2009) Fast Statistical Alignment. *PLoS Computational Biology.* 5:e1000392). In an embodiment, the subject disclosure relates to calculating percent identity between two polynucleotides or amino acid sequences using the Geneious alignment program (Kearse, M., et. al. (2012). *Geneious Basic: an integrated and extendable desktop software platform for the organization and analysis of sequence data. Bioinformatics,* 28(12), 1647-49). In an embodiment, the subject disclosure relates to calculating percent identity between two polynucleotides or amino acid sequences using the Kalign alignment program (Lassmann, T. & Sonnhammer, E. Kalign—an accurate and fast multiple sequence alignment algorithm. *BMC Bioinformatics* 2005 6:298). In an embodiment, the subject disclosure relates to calculating percent identity between two polynucleotides or amino acid sequences using the MAVID alignment program (Bray, N. & Pachter, L. MAVID: Constrained Ancestral Alignment of Multiple Sequences. *Genome Res.* 2004 April; 14(4): 693-99). In an embodiment, the subject disclosure relates to calculating percent identity between two polynucleotides or amino acid sequences using the MSA alignment program (Lipman, D J, et. al. A tool for multiple sequence alignment. *Proc. Nat'l Acad. Sci.* USA. 1989; 86:4412-15). In an embodiment, the subject disclosure relates to calculating percent identity between two polynucleotides or amino acid sequences using the MultAlin alignment program (Corpet, F., Multiple sequence alignment with hierarchical clustering. *Nucl. Acids Res.,* 1988, 16(22), 10881-90). In an embodiment, the subject disclosure relates to calculating percent identity between two polynucleotides or amino acid sequences using the LAGAN or MLAGAN alignment programs (Brudno, et. al. LAGAN and Multi-LAGAN: efficient tools for large-scale multiple alignment of genomic DNA. *Genome Research* 2003 April; 13(4): 721-31). In an embodiment, the subject disclosure relates to calculating percent identity between two polynucleotides or amino acid sequences using the Opal alignment program (Wheeler, T. J., & Kececiouglu, J. D. Multiple alignment by aligning alignments. Proceedings of the 15th ISCB conference on Intelligent Systems for Molecular Biology. *Bioinformatics.* 23, i559-68, 2007). In an embodiment, the subject disclosure relates to calculating percent identity between two polynucleotides or amino acid sequences using the PicXAA suite of programs, including, but not limited to, PicXAA, PicXAA-R, PicXAA-Web, etc. (Mohammad, S., Sahraeian, E. & Yoon, B. PicXAA: greedy probabilistic construction of maximum expected accuracy alignment of multiple sequences. *Nucleic Acids Research.* 38(15):4917-28. 2010). In an embodiment, the subject disclosure relates to calculating percent identity between two polynucleotides or amino acid sequences using the PSAlign alignment program (SZE, S.-H., Lu, Y., & Yang, Q. (2006) A polynomial time solvable formulation of multiple sequence alignment *Journal of Computational Biology,* 13, 309-19). In an embodiment, the subject disclosure relates to calculating percent identity between two polynucleotides or amino acid sequences using the StatAlign alignment program (Novák, Á., et. al. (2008) StatAlign: an extendable software package for joint Bayesian estimation of alignments and evolutionary trees. *Bioinformatics,* 24(20):2403-04). In an embodiment, the subject disclosure relates to calculating percent identity between two polynucleotides or amino acid sequences using the Gap alignment program of Needleman and Wunsch (Needleman and Wunsch, *Journal of Molecular Biology* 48:443-453, 1970). In an embodiment, the subject disclosure relates to calculating percent identity between two polynucleotides or amino acid sequences using the BestFit alignment program of Smith and Waterman (Smith and Waterman, *Advances in Applied Mathematics,* 2:482-489, 1981, Smith et al., *Nucleic Acids Research* 11:2205-2220, 1983). These programs produces biologically meaningful multiple sequence alignments of divergent sequences. The calculated best match alignments for the selected sequences are lined up so that identities, similarities, and differences can be seen.

The term "similarity" refers to a comparison between amino acid sequences, and takes into account not only identical amino acids in corresponding positions, but also functionally similar amino acids in corresponding positions. Thus similarity between polypeptide sequences indicates functional similarity, in addition to sequence similarity.

The term "homology" is sometimes used to refer to the level of similarity between two or more nucleic acid or amino acid sequences in terms of percent of positional identity (i.e., sequence similarity or identity). Homology also refers to the concept of evolutionary relatedness, often evidenced by similar functional properties among different nucleic acids or proteins that share similar sequences.

As used herein, the term "variants" means substantially similar sequences. For nucleotide sequences, naturally occurring variants can be identified with the use of well-known molecular biology techniques, such as, for example, with polymerase chain reaction (PCR) and hybridization techniques as outlined herein.

For nucleotide sequences, a variant comprises a deletion and/or addition of one or more nucleotides at one or more internal sites within the native polynucleotide and/or a substitution of one or more nucleotides at one or more sites in the native polynucleotide. As used herein, a "native" nucleotide sequence comprises a naturally occurring nucleotide sequence. For nucleotide sequences, naturally occurring variants can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence of the invention will have at least about 40%, 45%, 50%>, 55%, 60%, 65%, 70%, 75%, 80%, 85%, 90%, 91%, 92%, 93%, 94%, 95%, 96%, 97%, 98% o, 99% or more sequence identity to that particular nucleotide sequence as determined by sequence alignment programs and parameters described elsewhere herein. A biologically active variant of a nucleotide sequence of the invention may differ from that sequence by as few as 1-15 nucleic acid residues, as few as 1-10, such as 6-10, as few as 5, as few as 4, 3, 2, or even 1 nucleic acid residue.

As used herein the term "operably linked" relates to a first nucleic acid sequence is operably linked with a second nucleic acid sequence when the first nucleic acid sequence is in a functional relationship with the second nucleic acid sequence. For instance, a promoter is operably linked with a coding sequence when the promoter affects the transcription or expression of the coding sequence. When recombinantly produced, operably linked nucleic acid sequences are generally contiguous and, where necessary to join two protein-coding regions, in the same reading frame. However, elements need not be contiguous to be operably linked.

As used herein, the term "promoter" refers to a region of DNA that generally is located upstream (towards the 5' region of a gene) of a gene and is needed to initiate and drive transcription of the gene. A promoter may permit proper activation or repression of a gene that it controls. A promoter may contain specific sequences that are recognized by transcription factors. These factors may bind to a promoter DNA sequence, which results in the recruitment of RNA polymerase, an enzyme that synthesizes RNA from the coding region of the gene. The promoter generally refers to all gene regulatory elements located upstream of the gene, including, upstream promoters, 5' UTR, introns, and leader sequences.

As used herein, the term "upstream-promoter" refers to a contiguous polynucleotide sequence that is sufficient to direct initiation of transcription. As used herein, an upstream-promoter encompasses the site of initiation of transcription with several sequence motifs, which include TATA Box, initiator sequence, TFIIB recognition elements and other promoter motifs (Jennifer, E. F. et al., (2002) Genes & Dev., 16: 2583-2592). The upstream promoter provides the site of action to RNA polymerase II which is a multi-subunit enzyme with the basal or general transcription factors like, TFIIA, B, D, E, F and H. These factors assemble into a transcription pre initiation complex that catalyzes the synthesis of RNA from DNA template.

The activation of the upstream-promoter is done by the additional sequence of regulatory DNA sequence elements to which various proteins bind and subsequently interact with the transcription initiation complex to activate gene expression. These gene regulatory elements sequences interact with specific DNA-binding factors. These sequence motifs may sometimes be referred to as cis-elements. Such cis-elements, to which tissue-specific or development-specific transcription factors bind, individually or in combination, may determine the spatiotemporal expression pattern of a promoter at the transcriptional level. These cis-elements vary widely in the type of control they exert on operably linked genes. Some elements act to increase the transcription of operably-linked genes in response to environmental responses (e.g., temperature, moisture, and wounding). Other cis-elements may respond to developmental cues (e.g., germination, seed maturation, and flowering) or to spatial information (e.g., tissue specificity). See, for example, Langridge et al., (1989) Proc. Natl. Acad. Sci. USA 86:3219-23. These cis-elements are located at a varying distance from transcription start point, some cis-elements (called proximal elements) are adjacent to a minimal core promoter region while other elements can be positioned several kilobases upstream or downstream of the promoter (enhancers).

As used herein, the terms "5' untranslated region" or "5' UTR" is defined as the untranslated segment in the 5' terminus of pre-mRNAs or mature mRNAs. For example, on mature mRNAs, a 5' UTR typically harbors on its 5' end a 7-methylguanosine cap and is involved in many processes such as splicing, polyadenylation, mRNA export towards the cytoplasm, identification of the 5' end of the mRNA by the translational machinery, and protection of the mRNAs against degradation.

As used herein, the term "intron" refers to any nucleic acid sequence comprised in a gene (or expressed polynucleotide sequence of interest) that is transcribed but not translated. Introns include untranslated nucleic acid sequence within an expressed sequence of DNA, as well as the corresponding sequence in RNA molecules transcribed therefrom. A construct described herein can also contain sequences that enhance translation and/or mRNA stability such as introns. An example of one such intron is the first intron of gene II of the histone H3 variant of *Arabidopsis thaliana* or any other commonly known intron sequence. Introns can be used in combination with a promoter sequence to enhance translation and/or mRNA stability.

As used herein, the terms "transcription terminator" or "terminator" is defined as the transcribed segment in the 3' terminus of pre-mRNAs or mature mRNAs. For example, longer stretches of DNA beyond "polyadenylation signal" site is transcribed as a pre-mRNA. This DNA sequence usually contains transcription termination signal for the proper processing of the pre-mRNA into mature mRNA.

As used herein, the term "3' untranslated region" or "3' UTR" is defined as the untranslated segment in a 3' terminus of the pre-mRNAs or mature mRNAs. For example, on mature mRNAs this region harbors the poly-(A) tail and is known to have many roles in mRNA stability, translation initiation, and mRNA export. In addition, the 3' UTR is considered to include the polyadenylation signal and transcription terminator.

As used herein, the term "polyadenylation signal" designates a nucleic acid sequence present in mRNA transcripts that allows for transcripts, when in the presence of a poly-(A) polymerase, to be polyadenylated on the polyadenylation site, for example, located 10 to 30 bases downstream of the poly-(A) signal. Many polyadenylation signals are known in the art and are useful for the present invention. An exemplary sequence includes AAUAAA and variants thereof, as described in Loke J., et al., (2005) Plant Physiology 138(3); 1457-1468.

A "DNA binding transgene" is a polynucleotide coding sequence that encodes a DNA binding protein. The DNA binding protein is subsequently able to bind to another molecule. A binding protein can bind to, for example, a DNA molecule (a DNA-binding protein), a RNA molecule (an RNA-binding protein), and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding, and protein-binding activity.

Examples of DNA binding proteins include; meganucleases, zinc fingers, CRISPRs, and TALEN binding domains that can be "engineered" to bind to a predetermined nucleotide sequence. Typically, the engineered DNA binding proteins (e.g., zinc fingers, CRISPRs, or TALENs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP, CRISPR, and/or TALEN designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication Nos. 20110301073, 20110239315 and 20119145940.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; 6,534,261 and 6,794,136; see also WO 98/53058; WO 98/53059; WO 98/53060; WO 02/016536 and WO 03/016496.

In other examples, the DNA-binding domain of one or more of the nucleases comprises a naturally occurring or engineered (non-naturally occurring) TAL effector DNA binding domain. See, e.g., U.S. Patent Publication No. 20110301073, incorporated by reference in its entirety herein. The plant pathogenic bacteria of the genus Xanthomonas are known to cause many diseases in important crop plants. Pathogenicity of Xanthomonas depends on a conserved type III secretion (T3S) system which injects more than different effector proteins into the plant cell. Among these injected proteins are transcription activator-like (TALEN) effectors which mimic plant transcriptional activators and manipulate the plant transcriptome (see Kay et al., (2007) Science 318:648-651). These proteins contain a DNA binding domain and a transcriptional activation domain. One of the most well characterized TAL-effectors is AvrBs3 from Xanthomonas campestgris pv. Vesicatoria (see Bonas et al., (1989) Mol Gen Genet 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al., (2006) J Plant Physiol 163(3): 256-272). In addition, in the phytopathogenic bacteria Ralstonia solanacearum two genes, designated brg11 and hpx17 have been found that are homologous to the AvrBs3 family of Xanthomonas in the R. solanacearum biovar strain GMI1000 and in the biovar 4 strain RS1000 (See Heuer et al., (2007) Appl and Enviro Micro 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of Xanthomonas. See, e.g., U.S. Patent Publication No. 20110301073, incorporated by reference in its entirety.

Specificity of these TAL effectors depends on the sequences found in the tandem repeats. The repeated sequence comprises approximately 102 bp and the repeats are typically 91-100% homologous with each other (Bonas et al., ibid). Polymorphism of the repeats is usually located at positions 12 and 13 and there appears to be a one-to-one correspondence between the identity of the hypervariable diresidues at positions 12 and 13 with the identity of the contiguous nucleotides in the TAL-effector's target sequence (see Moscou and Bogdanove, (2009) Science 326:1501 and Boch et al., (2009) Science 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al., ibid). Engineered TAL proteins have been linked to a FokI cleavage half domain to yield a TAL effector domain nuclease fusion (TALEN) exhibiting activity in a yeast reporter assay (plasmid based target).

The CRISPR (Clustered Regularly Interspaced Short Palindromic Repeats)/Cas (CRISPR Associated) nuclease system is a recently engineered nuclease system based on a bacterial system that can be used for genome engineering. It is based on part of the adaptive immune response of many bacteria and Archaea. When a virus or plasmid invades a bacterium, segments of the invader's DNA are converted into CRISPR RNAs (crRNA) by the 'immune' response. This crRNA then associates, through a region of partial complementarity, with another type of RNA called tracrRNA to guide the Cas9 nuclease to a region homologous to the crRNA in the target DNA called a "protospacer." Cas9 cleaves the DNA to generate blunt ends at the double-stranded break (DSB) at sites specified by a 20-nucleotide guide sequence contained within the crRNA transcript. Cas9 requires both the crRNA and the tracrRNA for site specific DNA recognition and cleavage. This system has now been engineered such that the crRNA and tracrRNA can be combined into one molecule (the "single guide RNA"), and the crRNA equivalent portion of the single guide RNA can be engineered to guide the Cas9 nuclease to target any desired sequence (see Jinek et al., (2012) Science 337, pp. 816-821, Jinek et al., (2013), eLife 2:e00471, and David Segal, (2013) eLife 2:e00563). In other examples, the crRNA associates with the tracrRNA to guide the Cpf1 nuclease to a region homologous to the crRNA to cleave DNA with staggered ends (see Zetsche, Bernd, et al. *Cell* 163.3 (2015): 759-771.). Thus, the CRISPR/Cas system can be engineered to create a DSB at a desired target in a genome, and repair of the DSB can be influenced by the use of repair inhibitors to cause an increase in error prone repair.

In other examples, the DNA binding transgene/heterologous coding sequence is a site specific nuclease that comprises an engineered (non-naturally occurring) Meganuclease (also described as a homing endonuclease). The recognition sequences of homing endonucleases or meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al., (1997) *Nucleic Acids Res.* 25:3379-30 3388; Dujon et al., (1989) *Gene* 82:115-118; Perler et al., (1994) *Nucleic Acids Res.* 22, 11127; Jasin (1996) *Trends Genet.* 12:224-228; Gimble et al., (1996) *J. Mol. Biol.* 263:163-180; Argast et al., (1998) *J. Mol.* Biol. 280:345-353 and the New England Biolabs catalogue. In addition, the DNA-binding specificity of homing endonucleases and meganucleases can be engineered to bind non-natural target sites. See, for example, Chevalier et al., (2002) *Molec. Cell* 10:895-905; Epinat et al., (2003) *Nucleic Acids Res.* 5 31:2952-2962; Ashworth et al., (2006) *Nature* 441: 656-659; Paques et al., (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

As used herein, the term "transformation" encompasses all techniques that a nucleic acid molecule can be introduced into such a cell. Examples include, but are not limited to: transfection with viral vectors; transformation with plasmid vectors; electroporation; lipofection; microinjection (Mueller et al., (1978) *Cell* 15:579-85); *Agrobacterium*-mediated transfer; direct DNA uptake; WHISKERS™-mediated transformation; and microprojectile bombardment. These techniques may be used for both stable transformation and transient transformation of a plant cell. "Stable transformation" refers to the introduction of a nucleic acid fragment into a genome of a host organism resulting in genetically stable inheritance. Once stably transformed, the nucleic acid fragment is stably integrated in the genome of the host organism and any subsequent generation. Host organisms containing the transformed nucleic acid fragments are referred to as "transgenic" organisms. "Transient transformation" refers to the introduction of a nucleic acid fragment into the nucleus, or DNA-containing organelle, of a host organism resulting in gene expression without genetically stable inheritance.

An exogenous nucleic acid sequence. In one example, a transgene/heterologous coding sequence is a gene sequence (e.g., an herbicide-resistance gene), a gene encoding an industrially or pharmaceutically useful compound, or a gene encoding a desirable agricultural trait. In yet another example, the transgene/heterologous coding sequence is an antisense nucleic acid sequence, wherein expression of the antisense nucleic acid sequence inhibits expression of a target nucleic acid sequence. A transgene/heterologous coding sequence may contain regulatory sequences operably linked to the transgene/heterologous coding sequence (e.g., a promoter). In some embodiments, a polynucleotide sequence of interest is a transgene. However, in other embodiments, a polynucleotide sequence of interest is an endogenous nucleic acid sequence, wherein additional genomic copies of the endogenous nucleic acid sequence are desired, or a nucleic acid sequence that is in the antisense orientation with respect to the sequence of a target nucleic acid molecule in the host organism.

As used herein, the term a transgenic "event" is produced by transformation of plant cells with heterologous DNA, i.e., a nucleic acid construct that includes a transgene/heterologous coding sequence of interest, regeneration of a population of plants resulting from the insertion of the transgene/heterologous coding sequence into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that includes the genomic/transgene DNA. Even after repeated back-crossing to a recurrent parent, the inserted transgene/heterologous coding sequence DNA and flanking genomic DNA (genomic/transgene DNA) from the transformed parent is present in the progeny of the cross at the same chromosomal location. The term "event" also refers to DNA from the original transformant and progeny thereof comprising the inserted DNA and flanking genomic sequence immediately adjacent to the inserted DNA that would be expected to be transferred to a progeny that receives inserted DNA including the transgene/heterologous coding sequence of interest as the result of a sexual cross of one parental line that includes the inserted DNA (e.g., the original transformant and progeny resulting from selfing) and a parental line that does not contain the inserted DNA.

As used herein, the terms "Polymerase Chain Reaction" or "PCR" define a procedure or technique in which minute amounts of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.,* 51:263 (1987); Erlich, ed., *PCR Technology*, (Stockton Press, NY, 1989).

As used herein, the term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, which may include constituents which are co-factors or which affect conditions such as pH and the like at various suitable temperatures. A primer is preferably a single strand sequence, such that amplification efficiency is optimized, but double stranded sequences can be utilized.

As used herein, the term "probe" refers to an oligonucleotide that hybridizes to a target sequence. In the TaqMan® or TaqMan®-style assay procedure, the probe hybridizes to a portion of the target situated between the annealing site of the two primers. A probe includes about eight nucleotides, about ten nucleotides, about fifteen nucleotides, about twenty nucleotides, about thirty nucleotides, about forty nucleotides, or about fifty nucleotides. In some embodiments, a probe includes from about eight nucleotides to about fifteen nucleotides. A probe can further include a detectable label, e.g., a fluorophore (Texas-Red©, Fluorescein isothiocyanate, etc.,). The detectable label can be covalently attached directly to the probe oligonucleotide, e.g., located at the probe's 5' end or at the probe's 3' end. A probe including a fluorophore may also further include a quencher, e.g., Black Hole Quencher™, Iowa Black™, etc.

As used herein, the terms "restriction endonucleases" and "restriction enzymes" refer to bacterial enzymes, each of which cut double-stranded DNA at or near a specific nucleotide sequence. Type-2 restriction enzymes recognize and cleave DNA at the same site, and include but are not limited to XbaI, BamHI, HindIII, EcoRI, XhoI, SalI, KpnI, AvaI, PstI and SmaI.

As used herein, the term "vector" is used interchangeably with the terms "construct", "cloning vector" and "expression vector" and means the vehicle by which a DNA or RNA sequence (e.g. a foreign gene) can be introduced into a host cell, so as to transform the host and promote expression (e.g. transcription and translation) of the introduced sequence. A "non-viral vector" is intended to mean any vector that does not comprise a virus or retrovirus. In some embodiments a "vector" is a sequence of DNA comprising at least one origin of DNA replication and at least one selectable marker gene. Examples include, but are not limited to, a plasmid, cosmid, bacteriophage, bacterial artificial chromosome (BAC), or virus that carries exogenous DNA into a cell. A vector can also include one or more genes, antisense molecules, and/or selectable marker genes and other genetic elements known in the art. A vector may transduce, transform, or infect a cell, thereby causing the cell to express the nucleic acid molecules and/or proteins encoded by the vector.

The term "plasmid" defines a circular strand of nucleic acid capable of autosomal replication in either a prokaryotic or a eukaryotic host cell. The term includes nucleic acid which may be either DNA or RNA and may be single- or double-stranded. The plasmid of the definition may also include the sequences which correspond to a bacterial origin of replication.

As used herein, the term "selectable marker gene" as used herein defines a gene or other expression cassette which encodes a protein which facilitates identification of cells into which the selectable marker gene is inserted. For example a "selectable marker gene" encompasses reporter genes as well as genes used in plant transformation to, for example, protect plant cells from a selective agent or provide resistance/tolerance to a selective agent. In one embodiment only those cells or plants that receive a functional selectable marker are capable of dividing or growing under conditions having a selective agent. The phrase "marker-positive" refers to plants that have been transformed to include a selectable marker gene.

As used herein, the term "detectable marker" refers to a label capable of detection, such as, for example, a radioisotope, fluorescent compound, bioluminescent compound, a chemiluminescent compound, metal chelator, or enzyme. Examples of detectable markers include, but are not limited to, the following: fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In an embodiment, a detectable marker can be attached by spacer arms of various lengths to reduce potential steric hindrance.

As used herein, the terms "cassette", "expression cassette" and "gene expression cassette" refer to a segment of DNA that can be inserted into a nucleic acid or polynucleotide at specific restriction sites or by homologous recombination. As used herein the segment of DNA comprises a polynucleotide that encodes a polypeptide of interest, and the cassette and restriction sites are designed to ensure insertion of the cassette in the proper reading frame for transcription and translation. In an embodiment, an expression cassette can include a polynucleotide that encodes a polypeptide of interest and having elements in addition to the polynucleotide that facilitate transformation of a particular host cell. In an embodiment, a gene expression cassette may also include elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

As used herein a "linker" or "spacer" is a bond, molecule or group of molecules that binds two separate entities to one another. Linkers and spacers may provide for optimal spacing of the two entities or may further supply a labile linkage that allows the two entities to be separated from each other. Labile linkages include photocleavable groups, acid-labile moieties, base-labile moieties and enzyme-cleavable groups. The terms "polylinker" or "multiple cloning site" as used herein defines a cluster of three or more Type-2 restriction enzyme sites located within 10 nucleotides of one another on a nucleic acid sequence. In other instances the term "polylinker" as used herein refers to a stretch of nucleotides that are targeted for joining two sequences via any known seamless cloning method (i.e., Gibson Assembly®, NEBuilder HiFiDNA Assembly®, Golden Gate Assembly, BioBrick® Assembly, etc.). Constructs comprising a polylinker are utilized for the insertion and/or excision of nucleic acid sequences such as the coding region of a gene.

As used herein, the term "control" refers to a sample used in an analytical procedure for comparison purposes. A control can be "positive" or "negative". For example, where the purpose of an analytical procedure is to detect a differentially expressed transcript or polypeptide in cells or tissue, it is generally preferable to include a positive control, such as a sample from a known plant exhibiting the desired expression, and a negative control, such as a sample from a known plant lacking the desired expression.

As used herein, the term "plant" includes a whole plant and any descendant, cell, tissue, or part of a plant. A class of plant that can be used in the present invention is generally as broad as the class of higher and lower plants amenable to mutagenesis including angiosperms (monocotyledonous and dicotyledonous plants), gymnosperms, ferns and multicellular algae. Thus, "plant" includes dicot and monocot plants. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root.

A plant cell is the structural and physiological unit of the plant, comprising a protoplast and a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant cell" in embodiments herein.

As used herein, the term "small RNA" refers to several classes of non-coding ribonucleic acid (ncRNA). The term small RNA describes the short chains of ncRNA produced in bacterial cells, animals, plants, and fungi. These short chains of ncRNA may be produced naturally within the cell or may be produced by the introduction of an exogenous sequence that expresses the short chain or ncRNA. The small RNA sequences do not directly code for a protein, and differ in function from other RNA in that small RNA sequences are only transcribed and not translated. The small RNA sequences are involved in other cellular functions, including gene expression and modification. Small RNA molecules are usually made up of about 20 to 30 nucleotides. The small RNA sequences may be derived from longer precursors. The precursors form structures that fold back on each other in self-complementary regions; they are then processed by the nuclease Dicer in animals or DCL1 in plants.

Many types of small RNA exist either naturally or produced artificially, including microRNAs (miRNAs), short interfering RNAs (siRNAs), antisense RNA, short hairpin RNA (shRNA), and small nucleolar RNAs (snoRNAs). Certain types of small RNA, such as microRNA and siRNA, are important in gene silencing and RNA interference (RNAi). Gene silencing is a process of genetic regulation in which a gene that would normally be expressed is "turned off" by an intracellular element, in this case, the small RNA. The protein that would normally be formed by this genetic information is not formed due to interference, and the information coded in the gene is blocked from expression.

As used herein, the term "small RNA" encompasses RNA molecules described in the literature as "tiny RNA" (Storz, (2002) *Science* 296:1260-3; Illangasekare et al., (1999) *RNA* 5:1482-1489); prokaryotic "small RNA" (sRNA) (Wassarman et al., (1999) *Trends Microbiol.* 7:37-45); eukaryotic "noncoding RNA (ncRNA)"; "micro-RNA (miRNA)"; "small non-mRNA (snmRNA)"; "functional RNA (fRNA)"; "transfer RNA (tRNA)"; "catalytic RNA" [e.g., ribozymes, including self-acylating ribozymes (Illangaskare et al., (1999) *RNA* 5:1482-1489); "small nucleolar RNAs (snoRNAs)," "tmRNA" (a.k.a. "10S RNA," Muto et al., (1998) *Trends Biochem Sci.* 23:25-29; and Gillet et al., (2001) *Mol Microbiol.* 42:879-885); RNAi molecules including without limitation "small interfering RNA (siRNA)," "endoribonuclease-prepared siRNA (e-siRNA)," "short hairpin RNA (shRNA)," and "small temporally regulated RNA (stRNA)," "diced siRNA (d-siRNA)," and aptamers, oligonucleotides and other synthetic nucleic acids that comprise at least one uracil base.

Unless otherwise specifically explained, all technical and scientific terms used herein have the same meaning as commonly understood by those of ordinary skill in the art to which this disclosure belongs. Definitions of common terms in molecular biology can be found in, for example: Lewin, Genes V, Oxford University Press, 1994 (ISBN 0-19-854287-9); Kendrew et al. (eds.), *The Encyclopedia of Molecular Biology*, Blackwell Science Ltd., 1994 (ISBN 0-632-02182-9); and Meyers (ed.), *Molecular Biology and Biotechnology: A Comprehensive Desk Reference*, VCH Publishers, Inc., 1995 (ISBN 1-56081-569-8).

III. *Glycine max* Egg Cell Gene Regulatory Elements and Nucleic Acids Comprising the Same Provided are methods and compositions for using a promoter from a *Glycine max* Glyma19g07240 (Elongation factor-1 alpha) gene to express non-*Glycine max* egg cell transgenes in plant. In an embodiment, a promoter can be the *Glycine max* egg cell gene promoter of SEQ ID NO:2.

In an embodiment, a polynucleotide is provided comprising a promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:2. In an embodiment, a promoter is a *Glycine max* egg cell gene promoter comprising a polynucleotide of at least 80%, 85%, 90%, 91%, 92%, 93%, 94%, 95%, 96%, 97%, 98%, 99%, 99.5%, 99.8%, or 100% identity to the polynucleotide of SEQ ID NO:2. In an embodiment, an isolated polynucleotide is provided comprising at least 80%, 85%, 90%, 91%, 92%, 93%, 94%, 95%, 96%, 97%, 98%, 99%, 99.5%, 99.8%, or 100% identity to the polynucleotide of SEQ ID NO:2. In an embodiment, a nucleic acid vector is provided comprising a *Glycine max* egg cell promoter of SEQ ID NO:2. In an embodiment, a polynucleotide is provided comprising a *Glycine max* egg cell promoter that is operably linked to a polylinker. In an embodiment, a gene expression cassette is provided comprising a *Glycine max* egg cell promoter that is operably linked to a non-*Glycine max* egg cell transgene. In an embodiment, a nucleic acid vector is provided comprising a *Glycine max* egg cell promoter that is operably linked to a non-*Glycine max* egg cell transgene. In one embodiment, the promoter consists of SEQ ID NO:2. In an illustrative embodiment, a nucleic acid vector comprises a *Glycine max* egg cell promoter that is operably linked to a transgene, wherein the transgene/heterologous coding sequence can be an insecticidal resistance transgene, an herbicide tolerance transgene, a nitrogen use efficiency transgene, a water use efficiency transgene, a nutritional quality transgene, a DNA binding transgene, a small RNA transgene, selectable marker transgene, or combinations thereof.

In an embodiment, a nucleic acid vector comprises a gene expression cassette as disclosed herein. In an embodiment, a vector can be a plasmid, a cosmid, a bacterial artificial chromosome (BAC), a bacteriophage, a virus, or an excised polynucleotide fragment for use in direct transformation or gene targeting such as a donor DNA.

Transgene expression may also be regulated by a 5' UTR region located downstream of the promoter sequence. Both a promoter and a 5' UTR can regulate transgene/heterologous coding sequence expression. While a promoter is necessary to drive transcription, the presence of a 5' UTR can increase expression levels resulting in mRNA transcript for translation and protein synthesis. A 5' UTR gene region aids stable expression of a transgene. In a further embodiment an 5' UTR is operably linked to a *Glycine max* egg cell promoter. In an illustrative embodiment, a nucleic acid vector comprises a *Glycine max* egg cell promoter of SEQ ID NO:2 further comprising a 5' UTR that is operably linked to a transgene, wherein the transgene/heterologous coding sequence can be an insecticidal resistance transgene, an herbicide tolerance transgene, a nitrogen use efficiency transgene, a water use efficiency transgene, a nutritional quality transgene, a DNA binding transgene, a small RNA transgene, selectable marker transgene, or combinations thereof.

Transgene expression may also be regulated by an intron region located downstream of the promoter sequence. Both a promoter and an intron can regulate transgene/heterologous coding sequence expression. While a promoter is necessary to drive transcription, the presence of an intron can increase expression levels resulting in mRNA transcript for translation and protein synthesis. An intron gene region aids stable expression of a transgene. In a further embodiment an intron is operably linked to a *Glycine max* egg cell promoter. In an illustrative embodiment, a nucleic acid vector comprises a *Glycine max* egg cell promoter of SEQ ID NO:2 further comprising an intron that is operably linked to a transgene, wherein the transgene/heterologous coding sequence can be an insecticidal resistance transgene, an herbicide tolerance transgene, a nitrogen use efficiency transgene, a water use efficiency transgene, a nutritional quality transgene, a DNA binding transgene, a small RNA transgene, selectable marker transgene, or combinations thereof.

In accordance with one embodiment a nucleic acid vector is provided comprising a recombinant gene expression cassette wherein the recombinant gene expression cassette comprises a *Glycine max* egg cell promoter operably linked to a polylinker sequence, a non-*Glycine max* egg cell gene or non-*Glycine max* egg cell transgene or combination thereof. In one embodiment the recombinant gene cassette comprises a *Glycine max* egg cell promoter operably linked to a non-*Glycine max* egg cell gene or transgene. In one embodiment the recombinant gene cassette comprises a *Glycine max* egg cell promoter as disclosed herein is operably linked to a polylinker sequence. The polylinker is operably linked to the *Glycine max* egg cell promoter in a manner such that insertion of a coding sequence into one of the restriction sites of the polylinker will operably link the coding sequence allowing for expression of the coding sequence when the vector is transformed or transfected into a host cell.

In accordance with one embodiment a nucleic acid vector is provided comprising a gene cassette that consists of a *Glycine max* egg cell promoter and a non-*Glycine max* egg cell gene. In an embodiment, the *Glycine max* egg cell promoter of SEQ ID NO: 2 is operably linked to the 5' end of the non-*Glycine max* egg cell gene or transgene. In a further embodiment the *Glycine max* egg cell promoter sequence comprises SEQ ID NO:2 or a sequence that has 80, 85, 90, 95, 99 or 100% sequence identity with SEQ ID NO:2. In accordance with one embodiment a nucleic acid vector is provided comprising a gene cassette that consists of a *Glycine max* egg cell promoter, a non-*Glycine max* egg cell gene, wherein the *Glycine max* egg cell promoter is operably linked to the 5' end of the non-*Glycine max* egg cell gene, and the *Glycine max* egg cell promoter sequence comprises SEQ ID NO:2 or a sequence that has 80, 85, 90, 95, 99 or 100% sequence identity with SEQ ID NO: 2. In a further embodiment the *Glycine max* egg cell promoter sequence consists of SEQ ID NO: 2, or a 1,089 bp sequence that has 80, 85, 90, 95, or 99% sequence identity with SEQ ID NO: 2.

A *Glycine max* egg cell promoter may also comprise one or more additional sequence elements. In some embodiments, a *Glycine max* egg cell promoter may comprise an exon (e.g., a leader or signal peptide such as a chloroplast transit peptide or ER retention signal). For example and without limitation, a *Glycine max* egg cell promoter may encode an exon incorporated into the *Glycine max* egg cell promoter as a further embodiment.

Further provided are methods and compositions for using a 3' UTR from a *Glycine max* Glyma19g07240 (Elongation factor-1 alpha) gene to terminate the expression of non-*Glycine max* egg cell transgenes in a plant. In an embodiment, a 3' UTR terminator can be the *Glycine max* egg cell 3' UTR of SEQ ID NO:3.

In an embodiment, a polynucleotide is provided comprising a 3' UTR, wherein the 3' UTR is at least 80%, 85%, 90%, 91%, 92%, 93%, 94%, 95%, 96%, 97%, 98%, 99%, 99.5%, 99.8%, or 100% identical to SEQ ID NO:3. In an embodiment, a 3' UTR is a *Glycine max* egg cell 3' UTR comprising a polynucleotide of at least 80%, 85%, 90%, 91%, 92%, 93%, 94%, 95%, 96%, 97%, 98%, 99%, 99.5%, 99.8%, or 100% identity to the polynucleotide of SEQ ID NO:3. In an embodiment, an isolated polynucleotide is provided comprising at least 80%, 85%, 90%, 91%, 92%, 93%, 94%, 95%, 96%, 97%, 98%, 99%, 99.5%, 99.8%, or 100% identity to the polynucleotide of SEQ ID NO:3. In an embodiment, a nucleic acid vector is provided comprising a *Glycine max* egg cell 3' UTR of SEQ ID NO:3. In an embodiment, a polynucleotide is provided comprising a *Glycine max* egg cell 3' UTR that is operably linked to a polylinker. In an embodiment, a gene expression cassette is provided comprising a *Glycine max* egg cell 3' UTR that is operably linked to a non-*Glycine max* egg cell transgene. In an embodiment, a nucleic acid vector is provided comprising a *Glycine max* egg cell 3' UTR that is operably linked to a non-*Glycine max* egg cell transgene. In one embodiment, the 3' UTR consists of SEQ ID NO:3. In an illustrative embodiment, a nucleic acid vector comprises a *Glycine max* egg cell gene 3' UTR that is operably linked to a transgene, wherein the transgene/heterologous coding sequence can be an insecticidal resistance transgene, an herbicide tolerance transgene, a nitrogen use efficiency transgene, a water use efficiency transgene, a nutritional quality transgene, a DNA binding transgene, a small RNA transgene, selectable marker transgene, or combinations thereof.

In accordance with one embodiment a nucleic acid vector is provided comprising a recombinant gene expression cassette wherein the recombinant gene expression cassette comprises a *Glycine max* egg cell transcription terminator containing 3'UTR operably linked to a polylinker sequence, a non-*Glycine max* egg cell gene or transgene/heterologous coding sequence or combination thereof. In one embodiment the recombinant gene cassette comprises a *Glycine max* egg cell transcription terminator containing 3'UTR operably linked to a non-*Glycine max* egg cell gene or transgene. In one embodiment the recombinant gene cassette comprises a *Glycine max* egg cell transcription terminator containing 3'UTR as disclosed herein is operably linked to a polylinker sequence. The polylinker is operably linked to the *Glycine max* egg cell transcription terminator containing 3'UTR in a manner such that insertion of a coding sequence into one of the restriction sites of the polylinker will operably link the coding sequence allowing for expression of the coding sequence when the vector is transformed or transfected into a host cell.

In accordance with one embodiment a nucleic acid vector is provided comprising a gene cassette that consists of a *Glycine max* egg cell transcription terminator containing 3'UTR and a non-*Glycine max* egg cell gene. In an embodiment, the *Glycine max* egg cell transcription terminator containing 3'UTR of SEQ ID NO:3 is operably linked to the Y end of the non-*Glycine max* egg cell gene or transgene. In a further embodiment the *Glycine max* egg cell transcription terminator containing 3'UTR sequence comprises SEQ ID NO:3 or a sequence that has 80, 85, 90, 95, 99 or 100% sequence identity with SEQ ID NO:3. In accordance with one embodiment a nucleic acid vector is provided comprising a gene cassette that consists of a *Glycine max* egg cell transcription terminator containing 3'UTR, a non-*Glycine max* egg cell gene, wherein the *Glycine max* egg cell transcription terminator containing 3'UTR is operably linked to the Y end of the non-*Glycine max* egg cell gene, and the *Glycine max* egg cell transcription terminator containing 3'UTR sequence comprises SEQ ID NO:3 or a sequence that has 80, 85, 90, 95, 99 or 100% sequence identity with SEQ ID NO:3. In a further embodiment the *Glycine max* egg cell transcription terminator containing 3'UTR sequence consists of SEQ ID NO:3, or a 739 bp sequence that has 80, 85, 90, 95, or 99% sequence identity with SEQ ID NO:3.

Further provided are methods and compositions for using a terminator from a *Glycine max* Glyma19g07240 (Elongation factor-1 alpha) gene to terminate the expression of non-*Glycine max* egg cell transgenes in a plant. In an embodiment, a terminator can be the *Glycine max* egg cell terminator of SEQ ID NO:3.

In an embodiment, a polynucleotide is provided comprising a terminator, wherein the terminator is at least 80%, 85%, 90%, 91%, 92%, 93%, 94%, 95%, 96%, 97%, 98%, 99%, 99.5%, 99.8%, or 100% identical to SEQ ID NO:3. In an embodiment, a terminator is a *Glycine max* egg cell terminator comprising a polynucleotide of at least 80%, 85%, 90%, 91%, 92%, 93%, 94%, 95%, 96%, 97%, 98%, 99%, 99.5%, 99.8%, or 100% identity to the polynucleotide of SEQ ID NO:3. In an embodiment, an isolated polynucleotide is provided comprising at least 80%, 85%, 90%, 91%, 92%, 93%, 94%, 95%, 96%, 97%, 98%, 99%, 99.5%, 99.8%, or 100% identity to the polynucleotide of SEQ ID NO:3. In an embodiment, a nucleic acid vector is provided comprising a *Glycine max* egg cell terminator of SEQ ID NO:3. In an embodiment, a polynucleotide is provided comprising a *Glycine max* egg cell terminator that is operably linked to a polylinker. In an embodiment, a gene expression cassette is provided comprising a *Glycine max* egg cell terminator that is operably linked to a non-*Glycine max* egg cell transgene. In an embodiment, a nucleic acid vector is provided comprising a *Glycine max* egg cell terminator that is operably linked to a non-*Glycine max* egg cell transgene. In one embodiment, the terminator consists of SEQ ID NO:3. In an illustrative embodiment, a nucleic acid vector comprises a *Glycine max* egg cell terminator that is operably linked to a transgene, wherein the transgene/heterologous coding sequence can be an insecticidal resistance transgene, an herbicide tolerance transgene, a nitrogen use efficiency transgene, a water use efficiency transgene, a nutritional quality transgene, a DNA binding transgene, a small RNA transgene, selectable marker transgene, or combinations thereof.

In accordance with one embodiment a nucleic acid vector is provided comprising a recombinant gene expression cassette wherein the recombinant gene expression cassette comprises a *Glycine max* egg cell terminator operably linked to a polylinker sequence, a non-*Glycine max* egg cell gene or transgene or combination thereof. In one embodiment the recombinant gene cassette comprises a *Glycine max* egg cell terminator operably linked to a non-*Glycine max* egg cell gene or transgene. In one embodiment the recombinant gene cassette comprises a *Glycine max* egg cell terminator as disclosed herein is operably linked to a polylinker sequence. The polylinker is operably linked to the *Glycine max* egg cell terminator in a manner such that insertion of a coding sequence into one of the restriction sites of the polylinker will operably link the coding sequence allowing for expression of the coding sequence when the vector is transformed or transfected into a host cell.

In accordance with one embodiment a nucleic acid vector is provided comprising a gene cassette that consists of a *Glycine max* egg cell terminator and a non-*Glycine max* egg cell gene. In an embodiment, the *Glycine max* egg cell terminator of SEQ ID NO:3 is operably linked to the Y end of the non-*Glycine max* egg cell gene or transgene. In a further embodiment the *Glycine max* egg cell terminator sequence comprises SEQ ID NO:3 or a sequence that has 80, 85, 90, 95, 99 or 100% sequence identity with SEQ ID NO:3. In accordance with one embodiment a nucleic acid vector is provided comprising a gene cassette that consists of a *Glycine max* egg cell terminator, a non-*Glycine max* egg cell gene, wherein the *Glycine max* egg cell terminator is operably linked to the 3' end of the non-*Glycine max* egg cell gene, and the *Glycine max* egg cell terminator sequence comprises SEQ ID NO:3 or a sequence that has 80, 85, 90, 95, 99 or 100% sequence identity with SEQ ID NO:3. In a further embodiment the *Glycine max* egg cell terminator sequence consists of SEQ ID NO:3, or a 897 bp sequence that has 80, 85, 90, 95, or 99% sequence identity with SEQ ID NO:3.

In one embodiment a nucleic acid construct is provided comprising a *Glycine max* egg cell promoter and a non-*Glycine max* egg cell gene and optionally one or more of the following elements:
  a) a 5' untranslated region;
  b) an intron; and
  c) a 3' untranslated region,
wherein,
  the *Glycine max* egg cell promoter consists of SEQ ID NO:2 or a sequence having 95% sequence identity with SEQ ID NO:2; and
  the 3' UTR consists of a known 3' UTR, SEQ ID NO:3 or a sequence having 95% sequence identity with SEQ ID NO:3; further wherein said *Glycine max* egg cell promoter is operably linked to said transgene/heterologous coding sequence and each optional element, when present, is also operably linked to both the promoter and the transgene. In a further embodiment a transgenic cell is provided comprising the nucleic acid construct disclosed immediately above. In one embodiment the transgenic cell is a plant cell, and in a further embodiment a plant is provided wherein the plant comprises said transgenic cells.

In one embodiment a nucleic acid construct is provided comprising a *Glycine max* egg cell promoter and a non-*Glycine max* egg cell gene and optionally one or more of the following elements:
a) a 5' untranslated region;
b) an intron; and
c) a 3' terminator region, wherein,
the *Glycine max* egg cell promoter consists of SEQ ID NO:2 or a sequence having 95% sequence identity with SEQ ID NO:2; and
the 3' terminator consists of a known 3' terminator, SEQ ID NO:3 or a sequence having 95% sequence identity with SEQ ID NO:3; further wherein said *Glycine max* egg cell promoter is operably linked to said transgene/heterologous coding sequence and each optional element, when present, is also operably linked to both the promoter and the transgene. In a further embodiment a transgenic cell is provided comprising the nucleic acid construct disclosed immediately above. In one embodiment the transgenic cell is a plant cell, and in a further embodiment a plant is provided wherein the plant comprises said transgenic cells.

Another aspect of the subject disclosure comprises a functional variant which differs in one or more nucleotides from those of the nucleotide sequences comprising the regulatory element, provided herein. Such a variant is produced as the result of one or more modifications (e.g., deletion, rearrangement, or insertion) of the nucleotide sequences comprising the sequence described herein. For example, fragments and variants of the *Glycine max* egg cell promoter sequence of SEQ ID NO: 2 may be used in a DNA construct or in a gene expression cassette to drive expression of a heterologous coding sequence. As used herein, the term "fragment" refers to a portion of the nucleic acid sequence. Fragments of *Glycine max* egg cell promoter sequence of SEQ ID NO: 2 may retain the biological activity of initiating transcription, more particularly driving transcription in a ovule preferred tissue expressed manner. Alternatively, fragments of a nucleotide sequence which are useful as hybridization probes may not necessarily retain biological activity. Fragments of a nucleotide sequence for the promoter region of the *Glycine max* egg cell promoter sequence of SEQ ID NO:2 may range from at least about 20 nucleotides, about 50 nucleotides, about 100 nucleotides, up to the full-length nucleotide sequence of the invention for the promoter region of the gene.

A biologically active portion of a *Glycine max* egg cell promoter sequence of SEQ ID NO:2 can be prepared by isolating a portion of the *Glycine max* egg cell promoter sequence of SEQ ID NO:2, and assessing the promoter activity of the portion. Nucleic acid molecules that are fragments of an *Glycine max* egg cell promoter nucleotide sequence comprise at least about 16, 50, 75, 100, 150, 200, 250, 300, 350, 400, 450, 500, 550, 600, 650, 700, 800, 900, 1000, 1100, 1200, 1300, 1400, 1500, 1550, 1600, 1650, or 1700 nucleotides, or up to the number of nucleotides present in a full-length *Glycine max* egg cell promoter sequence disclosed herein.

Variant nucleotide sequences also encompass sequences derived from a mutagenic and recombinogenic procedure such as DNA shuffling. With such a procedure, *Glycine max* egg cell promoter nucleotide sequences of SEQ ID NO:2 can be manipulated to create a new *Glycine max* egg cell promoter. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) Proc. Natl. Acad. Sci. USA i: 10747-10751; Stemmer (1994) Nature 570:389-391; Crameri et al. (1997) Nature Biotech. 75:436-438; Moore et al. (1997) J. Mol. Biol. 272:336-347; Zhang et al. (1997) Proc. Natl. Acad. Sci. USA £4:4504-4509; Crameri et al. (1998) Nature 527:288-291; and U.S. Pat. Nos. 5,605,793 and 5,837,458.

The nucleotide sequences of the subject disclosure can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire *Glycine max* egg cell promoter sequence set forth herein or to fragments thereof are encompassed by the present invention.

In a PCR approach, oligonucleotide primers can be designed for use in PCR reactions to amplify corresponding DNA sequences from genomic DNA extracted from any plant of interest. Methods for designing PCR primers and PCR cloning are generally known in the art and are disclosed in Sambrook et al. (1989) Molecular Cloning: A Laboratory Manual (2d ed., Cold Spring Harbor Laboratory Press, Plainview, New York), hereinafter Sambrook. See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments from a chosen organism. The hybridization probes may be labeled with a detectable group such as $P^{32}$ or any other detectable marker. Thus, for example, probes for hybridization can be made by labeling synthetic oligonucleotides based on the *Glycine max* egg cell promoter sequence of the invention. Methods for preparation of probes for hybridization and for construction of genomic libraries are generally known in the art and are disclosed in Sambrook. For example, the entire *Glycine max* egg cell promoter sequence disclosed herein, or one or more portions thereof, may be used as a probe capable of specifically hybridizing to corresponding *Glycine max* egg cell promoter sequences and messenger RNAs. To achieve specific hybridization under a variety of conditions, such probes include sequences that are unique among *Glycine max* egg cell promoter sequence and are at least about 10 nucleotides in length or at least about 20 nucleotides in length. Such probes may be used to amplify corresponding *Glycine max* egg cell promoter sequence from a chosen plant by PCR. This technique may be used to isolate additional coding sequences from a desired organism, or as a diagnostic assay to determine the presence of coding sequences in an organism. Hybridization techniques include hybridization screening of plated DNA libraries (either plaques or colonies; see, for example, Sambrook).

In accordance with one embodiment the nucleic acid vector further comprises a sequence encoding a selectable maker. In accordance with one embodiment the recombinant gene cassette is operably linked to an *Agrobacterium*

T-DNA border. In accordance with one embodiment the recombinant gene cassette further comprises a first and second T-DNA border, wherein the first T-DNA border is operably linked to one end of a gene construct, and the second T-DNA border is operably linked to the other end of a gene construct. The first and second *Agrobacterium* T-DNA borders can be independently selected from T-DNA border sequences originating from bacterial strains selected from the group consisting of a nopaline synthesizing *Agrobacterium* T-DNA border, an ocotopine synthesizing *Agrobacterium* T-DNA border, a mannopine synthesizing *Agrobacterium* T-DNA border, a succinamopine synthesizing *Agrobacterium* T-DNA border, or any combination thereof. In one embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene/heterologous coding sequence operably linked to a sequence selected from SEQ ID NO:2 or a sequence having 80, 85, 90, 95, or 99% sequence identity with SEQ ID NO:2. In another embodiment, the first and second *Agrobacterium* T-DNA borders can be independently selected from T-DNA border sequences originating from bacterial strains selected from the group consisting of a nopaline synthesizing *Agrobacterium* T-DNA border, an ocotopine synthesizing *Agrobacterium* T-DNA border, a mannopine synthesizing *Agrobacterium* T-DNA border, a succinamopine synthesizing *Agrobacterium* T-DNA border, or any combination thereof. In an embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene/heterologous coding sequence operably linked to a sequence selected from SEQ ID NO:3 or a sequence having 80, 85, 90, 95, or 99% sequence identity with SEQ ID NO:3. In one embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene/heterologous coding sequence operably linked to a sequence selected from SEQ ID NO:3 or a sequence having 80, 85, 90, 95, or 99% sequence identity with SEQ ID NO:3. In one embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene/heterologous coding sequence operably linked to a sequence selected from SEQ ID NO:3 or a sequence having 80, 85, 90, 95, or 99% sequence identity with SEQ ID NO:3.

Transgenes of interest that are suitable for use in the present disclosed constructs include, but are not limited to, coding sequences that confer (1) resistance to pests or disease, (2) tolerance to herbicides, (3) value added agronomic traits, such as; yield improvement, nitrogen use efficiency, water use efficiency, and nutritional quality, (4) binding of a protein to DNA in a site specific manner, (5) expression of small RNA, and (6) selectable markers. In accordance with one embodiment, the transgene/heterologous coding sequence encodes a selectable marker or a gene product conferring insecticidal resistance, herbicide tolerance, small RNA expression, nitrogen use efficiency, water use efficiency, or nutritional quality.

1. Insect Resistance

Various insect resistance genes can be operably linked to the *Glycine max* egg cell promoter comprising SEQ ID NO: 2, or a sequence that has 80, 85, 90, 95 or 99% sequence identity with SEQ ID NO: 2. Likewise, the insect resistance genes can be operably linked to the *Glycine max* egg cell 3' UTR comprising SEQ ID NO:3, or a sequence that has 80, 85, 90, 95 or 99% sequence identity with SEQ ID NO:3. Furthermore, the insect resistance genes can be operably linked to the *Glycine max* egg cell terminator comprising SEQ ID NO:3, or a sequence that has 80, 85, 90, 95 or 99% sequence identity with SEQ ID NO:3. The operably linked sequences can then be incorporated into a chosen vector to allow for identification and selection of transformed plants ("transformants"). Exemplary insect resistance coding sequences are known in the art. As embodiments of insect resistance coding sequences that can be operably linked to the regulatory elements of the subject disclosure, the following traits are provided. Coding sequences that provide exemplary Lepidopteran insect resistance include: cry1A; cry1A.105; cry1Ab; cry1Ab(truncated); cry1Ab-Ac (fusion protein); cry1Ac (marketed as Widestrike®); cry1C; cry1F (marketed as Widestrike@); cry1Fa2; cry2Ab2; cry2Ae; cry9C; mocry1F; pinII (protease inhibitor protein); vip3A (a); and vip3Aa20. Coding sequences that provide exemplary Coleopteran insect resistance include: cry34Ab1 (marketed as Herculex®); cry35Ab1 (marketed as Herculex®); cry3A; cry3Bb1; dvsnf7; and mcry3A. Coding sequences that provide exemplary multi-insect resistance include ecry31.Ab. The above list of insect resistance genes is not meant to be limiting. Any insect resistance genes are encompassed by the present disclosure.

2. Herbicide Tolerance

Various herbicide tolerance genes can be operably linked to the *Glycine max* egg cell promoter comprising SEQ ID NO: 2, or a sequence that has 80, 85, 90, 95 or 99% sequence identity with SEQ ID NO: 2. Likewise, the insect resistance genes can be operably linked to the *Glycine max* egg cell 3' UTR comprising SEQ ID NO:3, or a sequence that has 80, 85, 90, 95 or 99% sequence identity with SEQ ID NO:3. Furthermore, the insect resistance genes can be operably linked to the *Glycine max* egg cell terminator comprising SEQ ID NO:3, or a sequence that has 80, 85, 90, 95 or 99% sequence identity with SEQ ID NO:3. The operably linked sequences can then be incorporated into a chosen vector to allow for identification and selection of transformed plants ("transformants"). Exemplary herbicide tolerance coding sequences are known in the art. As embodiments of herbicide tolerance coding sequences that can be operably linked to the regulatory elements of the subject disclosure, the following traits are provided. The glyphosate herbicide contains a mode of action by inhibiting the EPSPS enzyme (5-enolpyruvylshikimate-3-phosphate synthase). This enzyme is involved in the biosynthesis of aromatic amino acids that are essential for growth and development of plants. Various enzymatic mechanisms are known in the art that can be utilized to inhibit this enzyme. The genes that encode such enzymes can be operably linked to the gene regulatory elements of the subject disclosure. In an embodiment, selectable marker genes include, but are not limited to genes encoding glyphosate resistance genes include: mutant EPSPS genes such as 2mEPSPS genes, cp4 EPSPS genes, mEPSPS genes, dgt-28 genes; aroA genes; and glyphosate degradation genes such as glyphosate acetyl transferase genes (gat) and glyphosate oxidase genes (gox). These traits are currently marketed as Gly-Tol™, Optimum@ GAT@, Agrisure® GT and Roundup Ready@. Resistance genes for glufosinate and/or bialaphos compounds include dsm-2, bar and pat genes. The bar and pat traits are currently marketed as LibertyLink®. Also included are tolerance genes that provide resistance to 2,4-D such as aad-1 genes (it should be noted that aad-1 genes have further activity on arloxyphenoxypropionate herbicides) and aad-12 genes (it should be noted that aad-12 genes have further activity on pyidyloxyacetate synthetic auxins). These traits are marketed as Enlist@ crop protection technology. Resistance genes for ALS inhibitors (sulfonylureas, imidazolinones, triazolopyrimidines, pyrimidinylthiobenzoates, and sulfonylaminocarbonyl-triazolinones) are known in the art. These resistance genes most commonly result from point mutations to the ALS encoding gene sequence. Other ALS inhibitor resistance genes include hra genes, the csr1-2 genes, Sr-HrA genes, and surB genes. Some of the traits are marketed under the tradename Clearfield@. Herbicides that inhibit HPPD include the pyrazolones such as pyrazoxyfen, benzofenap, and topramezone; triketones such as mesotrione, sulcotrione, tembotrione, benzobicyclon; and diketonitriles such as isoxaflutole. These exemplary HPPD herbicides can be tolerated by known traits. Examples of HPPD inhibitors include hppdPF W336 genes (for resistance to isoxaflutole) and avhppd-03 genes (for resistance to meostrione). An example of oxynil herbicide tolerant traits include the bxn gene, which has been showed to impart resistance to the herbicide/antibiotic bromoxynil. Resistance genes for dicamba include the dicamba monooxygenase gene (dmo) as disclosed in International PCT Publication No. WO 2008/105890. Resistance genes for PPO or PROTOX inhibitor type herbicides (e.g., acifluorfen, butafenacil, flupropazil, pentoxazone, carfentrazone, fluazolate, pyraflufen, aclonifen, azafenidin, flumioxazin, flumiclorac, bifenox, oxyfluorfen, lactofen, fomesafen, fluoroglycofen, and sulfentrazone) are known in the art. Exemplary genes conferring resistance to PPO include over expression of a wild-type *Arabidopsis thaliana* PPO enzyme (Lermontova I and Grimm B, (2000) Overexpression of plastidic protoporphyrinogen IX oxidase leads to resistance to the diphenyl-ether herbicide acifluorfen. *Plant Physiol* 122:75-83.), the *B. subtilis* PPO gene (Li, X. and Nicholl D. 2005. Development of PPO inhibitor-resistant cultures and crops. *Pest Manag. Sci.* 61:277-285 and Choi KW, Han O, Lee HJ, Yun YC, Moon YH, Kim MK, Kuk YI, Han SU and Guh JO, (1998) Generation of resistance to the diphenyl ether herbicide, oxyfluorfen, via expression of the *Bacillus subtilis* protoporphyrinogen oxidase gene in transgenic tobacco plants. *Biosci Biotechnol Biochem* 62:558-560.) Resistance genes for pyridinoxy or phenoxy proprionic acids and cyclohexones include the ACCase inhibitor-encoding genes (e.g., Acc1-S1, Accl-S2 and Accl-S3). Exemplary genes conferring resistance to cyclohexanediones and/or aryloxyphenoxypropanoic acid include haloxyfop, diclofop, fenoxyprop, fluazifop, and quizalofop. Finally, herbicides can inhibit photosynthesis, including triazine or benzonitrile are provided tolerance by psbA genes (tolerance to triazine), 1s+ genes (tolerance to triazine), and nitrilase genes (tolerance to benzonitrile). The above list of herbicide tolerance genes is not meant to be limiting. Any herbicide tolerance genes are encompassed by the present disclosure.

3. Agronomic Traits

Various agronomic trait genes can be operably linked to the *Glycine max* egg cell promoter comprising SEQ ID NO: 2, or a sequence that has 80, 85, 90, 95 or 99% sequence identity with SEQ ID NO: 2. Likewise, the insect resistance genes can be operably linked to the *Glycine max* egg cell 3' UTR comprising SEQ ID NO:3, or a sequence that has 80, 85, 90, 95 or 99% sequence identity with SEQ ID NO:3. Furthermore, the insect resistance genes can be operably linked to the *Glycine max* egg cell terminator comprising SEQ ID NO:3, or a sequence that has 80, 85, 90, 95 or 99% sequence identity with SEQ ID NO:3. The operably linked sequences can then be incorporated into a chosen vector to allow for identification and selection of transformed plants ("transformants"). Exemplary agronomic trait coding sequences are known in the art. As embodiments of agronomic trait coding sequences that can be operably linked to the regulatory elements of the subject disclosure, the following traits are provided. Delayed fruit softening as provided by the pg genes inhibit the production of polygalacturonase enzyme responsible for the breakdown of pectin molecules in the cell wall, and thus causes delayed softening of the fruit. Further, delayed fruit ripening/senescence of acc genes act to suppress the normal expression of the native acc synthase gene, resulting in reduced ethylene production and delayed fruit ripening. Whereas, the accd genes metabolize the precursor of the fruit ripening hormone ethylene, resulting in delayed fruit ripening. Alternatively, the sam-k genes cause delayed ripening by reducing S-adenosylmethionine (SAM), a substrate for ethylene production. Drought stress tolerance phenotypes as provided by cspB genes maintain normal cellular functions under water stress conditions by preserving RNA stability and translation. Another example includes the EcBetA genes that catalyze the production of the osmoprotectant compound glycine betaine conferring tolerance to water stress. In addition, the RmBetA genes catalyze the production of the osmoprotectant compound glycine betaine conferring tolerance to water stress. Photosynthesis and yield enhancement is provided with the bbx32 gene that expresses a protein that interacts with one or more endogenous transcription factors to regulate the plant's day/night physiological processes. Ethanol production can be increase by expression of the amy797E genes that encode a thermostable alpha-amylase enzyme that enhances bio-ethanol production by increasing the thermostability of amylase used in degrading starch. Finally, modified amino acid compositions can result by the expression of the cordapA genes that encode a dihydrodipicolinate synthase enzyme that increases the production of amino acid lysine. The above list of agronomic trait coding sequences is not meant to be limiting. Any agronomic trait coding sequence is encompassed by the present disclosure.

4. DNA Binding Proteins

Various DNA binding transgene/heterologous coding sequence genes/heterologous coding sequences can be operably linked to the *Glycine max* egg cell promoter comprising SEQ ID NO: 2, or a sequence that has 80, 85, 90, 95 or 99% sequence identity with SEQ ID NO: 2. Likewise, the insect resistance genes can be operably linked to the *Glycine max* egg cell 3' UTR comprising SEQ ID NO:3, or a sequence that has 80, 85, 90, 95 or 99% sequence identity with SEQ ID NO:3. Furthermore, the insect resistance genes can be operably linked to the *Glycine max* egg cell terminator comprising SEQ ID NO:3, or a sequence that has 80, 85, 90, 95 or 99% sequence identity with SEQ ID NO:3. The operably linked sequences can then be incorporated into a chosen vector to allow for identification and selectable of transformed plants ("transformants"). Exemplary DNA binding protein coding sequences are known in the art. As embodiments of DNA binding protein coding sequences that can be operably linked to the regulatory elements of the subject disclosure, the following types of DNA binding proteins can include; Zinc Fingers, TALENS, CRISPRS, and meganucleases. The above list of DNA binding protein coding sequences is not meant to be limiting. Any DNA binding protein coding sequences is encompassed by the present disclosure.

5. Small RNA

Various small RNA sequences can be operably linked to the *Glycine max* egg cell promoter comprising SEQ ID NO: 2, or a sequence that has 80, 85, 90, 95 or 99% sequence identity with SEQ ID NO: 2. Likewise, the insect resistance genes can be operably linked to the *Glycine max* egg cell 3' UTR comprising SEQ ID NO:3, or a sequence that has 80, 85, 90, 95 or 99% sequence identity with SEQ ID NO:3. Furthermore, the insect resistance genes can be operably linked to the *Glycine max* egg cell terminator comprising SEQ ID NO:3, or a sequence that has 80, 85, 90, 95 or 99% sequence identity with SEQ ID NO:3. The operably linked sequences can then be incorporated into a chosen vector to allow for identification and selection of transformed plants ("transformants"). Exemplary small RNA traits are known in the art. As embodiments of small RNA coding sequences that can be operably linked to the regulatory elements of the subject disclosure, the following traits are provided. For example, delayed fruit ripening/senescence of the anti-efe small RNA delays ripening by suppressing the production of ethylene via silencing of the ACO gene that encodes an ethylene-forming enzyme. The altered lignin production of ccomt small RNA reduces content of guanacyl (G) lignin by inhibition of the endogenous S-adenosyl-L-methionine: trans-caffeoyl CoA 3-O-methyltransferase (CCOMT gene). Further, the Black Spot Bruise Tolerance in *Solanum verrucosum* can be reduced by the Ppo5 small RNA which triggers the degradation of Ppo5 transcripts to block black spot bruise development. Also included is the dvsnf7 small RNA that inhibits Western Corn Rootworm with dsRNA containing a 240 bp fragment of the Western Corn Rootworm Snf7 gene. Modified starch/carbohydrates can result from small RNA such as the pPhL small RNA (degrades PhL transcripts to limit the formation of reducing sugars through starch degradation) and pR1 small RNA (degrades R1 transcripts to limit the formation of reducing sugars through starch degradation). Additional, benefits such as reduced acrylamide resulting from the asn1 small RNA that triggers degradation of Asn1 to impair asparagine formation and reduce polyacrylamide. Finally, the non-browning phenotype of pgas ppo suppression small RNA results in suppressing PPO to produce apples with a non-browning phenotype. The above list of small RNAs is not meant to be limiting. Any small RNA encoding sequences are encompassed by the present disclosure.

6. Selectable Markers

Various selectable markers also described as reporter genes can be operably linked to the *Glycine max* egg cell promoter comprising SEQ ID NO: 2, or a sequence that has 80, 85, 90, 95 or 99% sequence identity with SEQ ID NO: 2. Likewise, the insect resistance genes can be operably linked to the *Glycine max* egg cell 3' UTR comprising SEQ ID NO:3, or a sequence that has 80, 85, 90, 95 or 99% sequence identity with SEQ ID NO:3. Furthermore, the insect resistance genes can be operably linked to the *Glycine max* egg cell terminator comprising SEQ ID NO:3, or a sequence that has 80, 85, 90, 95 or 99% sequence identity with SEQ ID NO:3. The operably linked sequences can then be incorporated into a chosen vector to allow for identification and selectable of transformed plants ("transformants"). Many methods are available to confirm expression of selectable markers in transformed plants, including for example DNA sequencing and PCR (polymerase chain reaction), Southern blotting, RNA blotting, immunological methods for detection of a protein expressed from the vector. But, usually the reporter genes are observed through visual observation of proteins that when expressed produce a colored product. Exemplary reporter genes are known in the art and encode fl-glucuronidase (GUS), luciferase, green fluorescent protein (GFP), yellow fluorescent protein (YFP, Phi-YFP), red fluorescent protein (DsRFP, RFP, etc), pi-galactosidase, and the like (See Sambrook, et al., *Molecular Cloning: A Laboratory Manual*, Third Edition, Cold Spring Harbor Press, N.Y., 2001, the content of which is incorporated herein by reference in its entirety).

Selectable marker genes are utilized for selection of transformed cells or tissues. Selectable marker genes include genes encoding antibiotic resistance, such as those encoding neomycin phosphotransferase II (NEO), spectinomycin/streptinomycin resistance (AAD), and hygromycin phosphotransferase (HPT or HGR) as well as genes conferring resistance to herbicidal compounds. Herbicide resistance genes generally code for a modified target protein insensitive to the herbicide or for an enzyme that degrades or detoxifies the herbicide in the plant before it can act. For example, resistance to glyphosate has been obtained by using genes coding for mutant target enzymes, 5-enolpyruvylshikimate-3-phosphate synthase (EPSPS). Genes and mutants for EPSPS are well known, and further described below. Resistance to glufosinate ammonium, bromoxynil, and 2,4-dichlorophenoxyacetate (2,4-D) have been obtained by using bacterial genes encoding PAT or DSM-2, a nitrilase, an AAD-1, or an AAD-12, each of which are examples of proteins that detoxify their respective herbicides.

In an embodiment, herbicides can inhibit the growing point or meristem, including imidazolinone or sulfonylurea, and genes for resistance/tolerance of acetohydroxyacid synthase (AHAS) and acetolactate synthase (ALS) for these herbicides are well known. Glyphosate resistance genes include mutant 5-enolpyruvylshikimate-3-phosphate synthase (EPSPs) and dgt-28 genes (via the introduction of recombinant nucleic acids and/or various forms of in vivo mutagenesis of native EPSPs genes), aroA genes and glyphosate acetyl transferase (GAT) genes, respectively). Resistance genes for other phosphono compounds include bar and pat genes from *Streptomyces* species, including *Streptomyces hygroscopicus* and *Streptomyces* viridichromogenes, and pyridinoxy or phenoxy proprionic acids and cyclohexones (ACCase inhibitor-encoding genes). Exemplary genes conferring resistance to cyclohexanediones and/or aryloxyphenoxypropanoic acid (including haloxyfop, diclofop, fenoxyprop, fluazifop, quizalofop) include genes of acetyl coenzyme A carboxylase (ACCase); Acc1-S1, Acc1-S2 and Acc1-S3. In an embodiment, herbicides can inhibit photosynthesis, including triazine (psbA and 1s+ genes) or benzonitrile (nitrilase gene). Futhermore, such selectable markers can include positive selection markers such as phosphomannose isomerase (PMI) enzyme.

In an embodiment, selectable marker genes include, but are not limited to genes encoding: 2,4-D; neomycin phosphotransferase II; cyanamide hydratase; aspartate kinase; dihydrodipicolinate synthase; tryptophan decarboxylase; dihydrodipicolinate synthase and desensitized aspartate kinase; bar gene; tryptophan decarboxylase; neomycin phosphotransferase (NEO); hygromycin phosphotransferase (HPT or HYG); dihydrofolate reductase (DHFR); phosphinothricin acetyltransferase; 2,2-dichloropropionic acid dehalogenase; acetohydroxyacid synthase; 5-enolpyruvylshikimate-phosphate synthase (aroA); haloarylnitrilase; acetyl-coenzyme A carboxylase; dihydropteroate synthase (sul I); and 32 kD photosystem II polypeptide (psbA). An embodiment also includes selectable marker genes encoding resistance to: chloramphenicol; methotrexate; hygromycin; spectinomycin; bromoxynil; glyphosate; and phosphinothricin. The above list of selectable marker genes is not meant to be limiting. Any reporter or selectable marker gene are encompassed by the present disclosure.

In some embodiments the coding sequences are synthesized for optimal expression in a plant. For example, in an embodiment, a coding sequence of a gene has been modified by codon optimization to enhance expression in plants. An insecticidal resistance transgene, an herbicide tolerance transgene, a nitrogen use efficiency transgene, a water use efficiency transgene, a nutritional quality transgene, a DNA binding transgene, or a selectable marker transgene/heterologous coding sequence can be optimized for expression in a particular plant species or alternatively can be modified for optimal expression in dicotyledonous or monocotyledonous plants. Plant preferred codons may be determined from the codons of highest frequency in the proteins expressed in the largest amount in the particular plant species of interest. In an embodiment, a coding sequence, gene, heterologous coding sequence or transgene/heterologous coding sequence is designed to be expressed in plants at a higher level resulting in higher transformation efficiency. Methods for plant optimization of genes are well known. Guidance regarding the optimization and production of synthetic DNA sequences can be found in, for example, WO2013016546, WO2011146524, WO1997013402, U.S. Pat. Nos. 6,166,302, and 5,380,831, herein incorporated by reference.

Transformation

Suitable methods for transformation of plants include any method by which DNA can be introduced into a cell, for example and without limitation: electroporation (see, e.g., U.S. Pat. No. 5,384,253); micro-projectile bombardment (see, e.g., U.S. Pat. Nos. 5,015,580, 5,550,318, 5,538,880, 6,160,208, 6,399,861, and 6,403,865); *Agrobacterium*-mediated transformation (see, e.g., U.S. Pat. Nos. 5,635,055, 5,824,877, 5,591,616; 5,981,840, and 6,384,301); and protoplast transformation (see, e.g., U.S. Pat. No. 5,508,184).

A DNA construct may be introduced directly into the genomic DNA of the plant cell using techniques such as agitation with silicon carbide fibers (see, e.g., U.S. Pat. Nos. 5,302,523 and 5,464,765), or the DNA constructs can be introduced directly to plant tissue using biolistic methods, such as DNA particle bombardment (see, e.g., Klein et al. (1987) *Nature* 327:70-73). Alternatively, the DNA construct can be introduced into the plant cell via nanoparticle transformation (see, e.g., US Patent Publication No. 20090104700, which is incorporated herein by reference in its entirety).

In addition, gene transfer may be achieved using non-*Agrobacterium* bacteria or viruses such as *Rhizobium* sp. NGR234, Sinorhizoboium *meliloti, Mesorhizobium loti,* potato virus X, cauliflower mosaic virus and cassava vein mosaic virus and/or tobacco mosaic virus, See, e.g., Chung et al. (2006) *Trends Plant Sci.* 11(1):1-4.

Through the application of transformation techniques, cells of virtually any plant species may be stably transformed, and these cells may be developed into transgenic plants by well-known techniques. For example, techniques that may be particularly useful in the context of cotton transformation are described in U.S. Pat. Nos. 5,846,797, 5,159,135, 5,004,863, and 6,624,344; techniques for transforming *Brassica* plants in particular are described, for example, in U.S. Pat. No. 5,750,871; techniques for transforming soy bean are described, for example, in U.S. Pat. No. 6,384,301; and techniques for transforming *Zea mays* are described, for example, in U.S. Pat. Nos. 7,060,876 and 5,591,616, and International PCT Publication WO 95/06722.

After effecting delivery of an exogenous nucleic acid to a recipient cell, a transformed cell is generally identified for further culturing and plant regeneration. In order to improve the ability to identify transformants, one may desire to employ a selectable marker gene with the transformation vector used to generate the transformant. In an illustrative embodiment, a transformed cell population can be assayed by exposing the cells to a selective agent or agents, or the cells can be screened for the desired marker gene trait.

Cells that survive exposure to a selective agent, or cells that have been scored positive in a screening assay, may be cultured in media that supports regeneration of plants. In an embodiment, any suitable plant tissue culture media may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

Molecular Confirmation

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed plants and plant cells can also be identified by screening for the activities of any visible marker genes (e.g., the β-glucuronidase, luciferase, or green fluorescent protein genes) that may be present on the recombinant nucleic acid constructs. Such selection and screening methodologies are well known to those skilled in the art. Molecular confirmation methods that can be used to identify transgenic plants are known to those with skill in the art. Several exemplary methods are further described below.

Molecular Beacons have been described for use in sequence detection. Briefly, a FRET oligonucleotide probe is designed that overlaps the flanking genomic and insert DNA junction. The unique structure of the FRET probe results in it containing a secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe(s) to the target sequence results in the removal of the probe secondary structure and spatial separation of the fluorescent and quenching moieties. A fluorescent signal indicates the presence of the flanking genomic/transgene insert sequence due to successful amplification and hybridization. Such a molecular beacon assay for detection of as an amplification reaction is an embodiment of the subject disclosure.

Hydrolysis probe assay, otherwise known as TAQMAN® (Life Technologies, Foster City, Calif.), is a method of detecting and quantifying the presence of a DNA sequence. Briefly, a FRET oligonucleotide probe is designed with one oligo within the transgene/heterologous coding sequence and one in the flanking genomic sequence for event-specific detection. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization. Such a hydrolysis probe assay for detection of as an amplification reaction is an embodiment of the subject disclosure.

KASPar® assays are a method of detecting and quantifying the presence of a DNA sequence. Briefly, the genomic DNA sample comprising the integrated gene expression cassette polynucleotide is screened using a polymerase chain reaction (PCR) based assay known as a KASPar® assay system. The KASPar® assay used in the practice of the subject disclosure can utilize a KASPar® PCR assay mixture which contains multiple primers. The primers used in the PCR assay mixture can comprise at least one forward primers and at least one reverse primer. The forward primer contains a sequence corresponding to a specific region of the DNA polynucleotide, and the reverse primer contains a sequence corresponding to a specific region of the genomic sequence. In addition, the primers used in the PCR assay mixture can comprise at least one forward primers and at least one reverse primer. For example, the KASPar® PCR assay mixture can use two forward primers corresponding to two different alleles and one reverse primer. One of the forward primers contains a sequence corresponding to specific region of the endogenous genomic sequence. The second forward primer contains a sequence corresponding to a specific region of the DNA polynucleotide. The reverse primer contains a sequence corresponding to a specific region of the genomic sequence. Such a KASPar® assay for detection of an amplification reaction is an embodiment of the subject disclosure.

In some embodiments the fluorescent signal or fluorescent dye is selected from the group consisting of a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye.

In other embodiments the amplification reaction is run using suitable second fluorescent DNA dyes that are capable of staining cellular DNA at a concentration range detectable by flow cytometry, and have a fluorescent emission spectrum which is detectable by a real time thermocycler. It should be appreciated by those of ordinary skill in the art that other nucleic acid dyes are known and are continually being identified. Any suitable nucleic acid dye with appropriate excitation and emission spectra can be employed, such as YO-PRO-1®, SYTOX Green®, SYBR Green I®, SYTO11®, SYTO12®, SYTO13®, BOBO@, YOYO®, and TOTO®. In one embodiment, a second fluorescent DNA dye is SYTO13® used at less than 10 PM, less than 4 µM, or less than 2.7 µM.

In further embodiments, Next Generation Sequencing (NGS) can be used for detection. As described by Brautigma et al., 2010, DNA sequence analysis can be used to determine the nucleotide sequence of the isolated and amplified fragment. The amplified fragments can be isolated and sub-cloned into a vector and sequenced using chain-terminator method (also referred to as Sanger sequencing) or Dye-terminator sequencing. In addition, the amplicon can be sequenced with Next Generation Sequencing. NGS technologies do not require the sub-cloning step, and multiple sequencing reads can be completed in a single reaction. Three NGS platforms are commercially available, the Genome Sequencer FLX™ from 454 Life Sciences/Roche, the Illumina Genome Analyser™ from Solexa and Applied Biosystems' SOLiD™ (acronym for: 'Sequencing by Oligo Ligation and Detection'). In addition, there are two single molecule sequencing methods that are currently being developed. These include the true Single Molecule Sequencing (tSMS) from Helicos Bioscience™ and the Single Molecule Real Time™ sequencing (SMRT) from Pacific Biosciences.

The Genome Sequencher FLX™ which is marketed by 454 Life Sciences/Roche is a long read NGS, which uses emulsion PCR and pyrosequencing to generate sequencing reads. DNA fragments of 300-800 bp or libraries containing fragments of 3-20 kb can be used. The reactions can produce over a million reads of about 250 to 400 bases per run for a total yield of 250 to 400 megabases. This technology produces the longest reads but the total sequence output per run is low compared to other NGS technologies.

The Illumina Genome Analyser™ which is marketed by Solexa™ is a short read NGS which uses sequencing by synthesis approach with fluorescent dye-labeled reversible terminator nucleotides and is based on solid-phase bridge PCR. Construction of paired end sequencing libraries containing DNA fragments of up to 10 kb can be used. The reactions produce over 100 million short reads that are 35-76 bases in length. This data can produce from 3-6 gigabases per run.

The Sequencing by Oligo Ligation and Detection (SOLiD) system marketed by Applied Biosystems™ is a short read technology. This NGS technology uses fragmented double stranded DNA that are up to 10 kb in length. The system uses sequencing by ligation of dye-labelled oligonucleotide primers and emulsion PCR to generate one billion short reads that result in a total sequence output of up to 30 gigabases per run.

tSMS of Helicos Bioscience™ and SMRT of Pacific Biosciences™ apply a different approach which uses single DNA molecules for the sequence reactions. The tSMS Helicos™ system produces up to 800 million short reads that result in 21 gigabases per run. These reactions are completed using fluorescent dye-labelled virtual terminator nucleotides that is described as a 'sequencing by synthesis' approach.

The SMRT Next Generation Sequencing system marketed by Pacific Biosciences™ uses a real time sequencing by synthesis. This technology can produce reads of up to 1,000 bp in length as a result of not being limited by reversible terminators. Raw read throughput that is equivalent to one-fold coverage of a diploid human genome can be produced per day using this technology.

In another embodiment, the detection can be completed using blotting assays, including Western blots, Northern blots, and Southern blots. Such blotting assays are commonly used techniques in biological research for the identification and quantification of biological samples. These assays include first separating the sample components in gels by electrophoresis, followed by transfer of the electrophoretically separated components from the gels to transfer membranes that are made of materials such as nitrocellulose, polyvinylidene fluoride (PVDF), or Nylon. Analytes can also be directly spotted on these supports or directed to specific regions on the supports by applying vacuum, capillary action, or pressure, without prior separation. The transfer membranes are then commonly subjected to a post-transfer treatment to enhance the ability of the analytes to be distinguished from each other and detected, either visually or by automated readers.

In a further embodiment the detection can be completed using an ELISA assay, which uses a solid-phase enzyme immunoassay to detect the presence of a substance, usually an antigen, in a liquid sample or wet sample. Antigens from the sample are attached to a surface of a plate. Then, a further specific antibody is applied over the surface so it can bind to the antigen. This antibody is linked to an enzyme, and, in the final step, a substance containing the enzyme's substrate is added. The subsequent reaction produces a detectable signal, most commonly a color change in the substrate.

Transgenic Plants

In an embodiment, a plant, plant tissue, or plant cell comprises a *Glycine max* egg cell promoter. In one embodiment a plant, plant tissue, or plant cell comprises the *Glycine max* egg cell promoter of a sequence selected from SEQ ID NO:2 or a sequence that has 80%, 85%, 90%, 95% or 99.5% sequence identity with a sequence selected from SEQ ID NO:2. In an embodiment, a plant, plant tissue, or plant cell comprises a gene expression cassette comprising a sequence selected from SEQ ID NO:2, or a sequence that has 80%, 85%, 90%, 95% or 99.5% sequence identity with a sequence selected from SEQ ID NO:2 that is operably linked to a non-*Glycine max* egg cell gene. In an illustrative embodiment, a plant, plant tissue, or plant cell comprises a gene expression cassette comprising a *Glycine max* egg cell promoter that is operably linked to a transgene or heterologous coding sequence, wherein the transgene or heterologous coding sequence can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In accordance with one embodiment a plant, plant tissue, or plant cell is provided wherein the plant, plant tissue, or plant cell comprises a *Glycine max* egg cell promoter derived sequence operably linked to a transgene, wherein the *Glycine max* egg cell promoter derived sequence comprises a sequence SEQ ID NO:2 or a sequence having 80%, 85%, 90%, 95% or 99.5% sequence identity with SEQ ID NO:2. In one embodiment a plant, plant tissue, or plant cell is provided wherein the plant, plant tissue, or plant cell comprises SEQ ID NO:2, or a sequence that has 80%, 85%, 90%, 95% or 99.5% sequence identity with SEQ ID NO:2 operably linked to a non-*Glycine max* egg cell gene. In one embodiment the plant, plant tissue, or plant cell is a dicotyledonous or monocotyledonous plant or a cell or tissue derived from a dicotyledonous or monocotyledonous plant. In one embodiment the plant is selected from the group consisting of *Zea mays*, wheat, rice, sorghum, oats, rye, bananas, sugar cane, soybean, cotton, sunflower, and canola. In one embodiment the plant is *Zea mays*. In another embodiment the plant is soybean (e.g., *Glycine max*). In accordance with one embodiment the plant, plant tissue, or plant cell comprises SEQ ID NO: 2 or a sequence having 80%, 85%, 90%, 95% or 99.5% sequence identity with SEQ ID NO:2 operably linked to a non-*Glycine max* egg cell gene. In one embodiment the plant, plant tissue, or plant cell comprises a promoter operably linked to a transgene/heterologous coding sequence wherein the promoter consists of SEQ ID NO:2 or a sequence having 80%, 85%, 90%, 95% or 99.5% sequence identity with SEQ ID NO:2. In accordance with one embodiment the gene construct comprising *Glycine max* egg cell promoter sequence operably linked to a transgene/heterologous coding sequence is incorporated into the genome of the plant, plant tissue, or plant cell.

In an embodiment, a plant, plant tissue, or plant cell comprises a *Glycine max* egg cell 3' UTR. In one embodiment a plant, plant tissue, or plant cell comprises the *Glycine max* egg cell 3' UTR of a sequence selected from SEQ ID NO:3 or a sequence that has 80%, 85%, 90%, 95% or 99.5% sequence identity with a sequence selected from SEQ ID NO:3. In an embodiment, a plant, plant tissue, or plant cell comprises a gene expression cassette comprising a sequence selected from SEQ ID NO:3, or a sequence that has 80%, 85%, 90%, 95% or 99.5% sequence identity with a sequence selected from SEQ ID NO:3 that is operably linked to a non-*Glycine max* egg cell gene. In an illustrative embodiment, a plant, plant tissue, or plant cell comprises a gene expression cassette comprising a *Glycine max* egg cell 3' UTR that is operably linked to a transgene, wherein the transgene/heterologous coding sequence can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In accordance with one embodiment a plant, plant tissue, or plant cell is provided wherein the plant, plant tissue, or plant cell comprises a *Glycine max* egg cell 3' UTR derived sequence operably linked to a transgene, wherein the *Glycine max* egg cell 3' UTR derived sequence comprises a sequence SEQ ID NO:3 or a sequence having 80%, 85%, 90%, 95% or 99.5% sequence identity with SEQ ID NO:3. In one embodiment a plant, plant tissue, or plant cell is provided wherein the plant, plant tissue, or plant cell comprises SEQ ID NO:3, or a sequence that has 80%, 85%, 90%, 95% or 99.5% sequence identity with SEQ ID NO:3 operably linked to a non-*Glycine max* egg cell gene. In one embodiment the plant, plant tissue, or plant cell is a dicotyledonous or monocotyledonous plant or a cell or tissue derived from a dicotyledonous or monocotyledonous plant. In one embodiment the plant is selected from the group consisting of *Zea mays*, wheat, rice, sorghum, oats, rye, bananas, sugar cane, soybean, cotton, sunflower, and canola. In one embodiment the plant is *Zea mays*. In another embodiment the plant is soybean (e.g,. *Glycine max*). In accordance with one embodiment the plant, plant tissue, or plant cell comprises SEQ ID NO:3 or a sequence having 80%, 85%, 90%, 95% or 99.5% sequence identity with SEQ ID NO:3 operably linked to a non-*Glycine max* egg cell gene. In one embodiment the plant, plant tissue, or plant cell comprises a 3' UTR operably linked to a transgene/heterologous coding sequence wherein the 3' UTR consists of SEQ ID NO:3 or a sequence having 80%, 85%, 90%, 95% or 99.5% sequence identity with SEQ ID NO:3. In accordance with one embodiment the gene construct comprising *Glycine max* egg cell gene 3' UTR sequence operably linked to a transgene/heterologous coding sequence is incorporated into the genome of the plant, plant tissue, or plant cell.

In an embodiment, a plant, plant tissue, or plant cell comprises a *Glycine max* egg cell terminator. In one embodiment a plant, plant tissue, or plant cell comprises the *Glycine max* egg cell terminator of a sequence selected from SEQ ID NO:3 or a sequence that has 80%, 85%, 90%, 95% or 99.5% sequence identity with a sequence selected from SEQ ID NO:3. In an embodiment, a plant, plant tissue, or plant cell comprises a gene expression cassette comprising a sequence selected from SEQ ID NO:3, or a sequence that has 80%, 85%, 90%, 95% or 99.5% sequence identity with a sequence selected from SEQ ID NO:3 that is operably linked to a non-*Glycine max* egg cell gene. In an illustrative embodiment, a plant, plant tissue, or plant cell comprises a gene expression cassette comprising a *Glycine max* egg cell terminator that is operably linked to a transgene, wherein the transgene/heterologous coding sequence can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In accordance with one embodiment a plant, plant tissue, or plant cell is provided wherein the plant, plant tissue, or plant cell comprises a *Glycine max* egg cell terminator derived sequence operably linked to a transgene, wherein the *Glycine max* egg cell terminator derived sequence comprises a sequence SEQ ID NO:3 or a sequence having 80%, 85%, 90%, 95% or 99.5% sequence identity with SEQ ID NO:3. In one embodiment a plant, plant tissue, or plant cell is provided wherein the plant, plant tissue, or plant cell comprises SEQ ID NO:3, or a sequence that has 80%, 85%, 90%, 95% or 99.5% sequence identity with SEQ ID NO:3 operably linked to a non-*Glycine max* egg cell gene. In one embodiment the plant, plant tissue, or plant cell is a dicotyledonous or monocotyledonous plant or a cell or tissue derived from a dicotyledonous or monocotyledonous plant. In one embodiment the plant is selected from the group consisting of *Zea mays*, wheat, rice, sorghum, oats, rye, bananas, sugar cane, soybean, cotton, sunflower, and canola. In one embodiment the plant is *Zea mays*. In another embodiment the plant is soybean (e.g,. *Glycine max*). In accordance with one embodiment the plant, plant tissue, or plant cell comprises SEQ ID NO:3 or a sequence having 80%, 85%, 90%, 95% or 99.5% sequence identity with SEQ ID NO:3 operably linked to a non-*Glycine max* egg cell gene. In one embodiment the plant, plant tissue, or plant cell comprises a terminator operably linked to a transgene/heterologous coding sequence wherein the terminator consists of SEQ ID NO:3 or a sequence having 80%, 85%, 90%, 95% or 99.5% sequence identity with SEQ ID NO:3. In accordance with one embodiment the gene construct comprising *Glycine max* egg cell gene terminator sequence operably linked to a transgene/heterologous coding sequence is incorporated into the genome of the plant, plant tissue, or plant cell.

In an embodiment, a plant, plant tissue, or plant cell according to the methods disclosed herein can be a dicotyledonous plant. The dicotyledonous plant, plant tissue, or plant cell can be, but not limited to alfalfa, rapeseed, canola, Indian mustard, Ethiopian mustard, soybean, sunflower, cotton, beans, broccoli, cabbage, cauliflower, celery, cucumber, eggplant, lettuce; melon, pea, pepper, peanut, potato, pumpkin, radish, spinach, sugarbeet, sunflower, tobacco, tomato, and watermelon.

One of skill in the art will recognize that after the exogenous sequence is stably incorporated in transgenic plants and confirmed to be operable, it can be introduced into other plants by sexual crossing. Any of a number of standard breeding techniques can be used, depending upon the species to be crossed.

The present disclosure also encompasses seeds of the transgenic plants described above, wherein the seed has the transgene/heterologous coding sequence or gene construct containing the gene regulatory elements of the subject disclosure. The present disclosure further encompasses the progeny, clones, cell lines or cells of the transgenic plants described above wherein said progeny, clone, cell line or cell has the transgene/heterologous coding sequence or gene construct containing the gene regulatory elements of the subject disclosure.

The present disclosure also encompasses the cultivation of transgenic plants described above, wherein the transgenic plant has the transgene/heterologous coding sequence or gene construct containing the gene regulatory elements of the subject disclosure. Accordingly, such transgenic plants may be engineered to, inter alia, have one or more desired traits or transgenic events containing the gene regulatory elements of the subject disclosure, by being transformed with nucleic acid molecules according to the invention, and may be cropped or cultivated by any method known to those of skill in the art.

Method of Expressing a Transgene

In an embodiment, a method of expressing at least one transgene/heterologous coding sequence in a plant comprises growing a plant comprising a *Glycine max* egg cell promoter operably linked to at least one transgene/heterologous coding sequence or a polylinker sequence. In an embodiment the *Glycine max* egg cell promoter consists of a sequence selected from SEQ ID NO:2 or a sequence that has 80%, 85%, 90%, 95% or 99.5% sequence identity with a sequence selected from SEQ ID NO:2. In an embodiment, a method of expressing at least one transgene/heterologous coding sequence in a plant comprising growing a plant comprising a *Glycine max* egg cell promoter operably linked to at least one transgene. In an embodiment, a method of expressing at least one transgene/heterologous coding sequence in a plant tissue or plant cell comprising culturing a plant tissue or plant cell comprising a *Glycine max* egg cell promoter operably linked to at least one transgene.

In an embodiment, a method of expressing at least one transgene/heterologous coding sequence in a plant comprises growing a plant comprising a gene expression cassette comprising a *Glycine max* egg cell promoter operably linked to at least one transgene. In one embodiment the *Glycine max* egg cell promoter consists of a sequence selected from SEQ ID NO:2 or a sequence that has 80%, 85%, 90%, 95% or 99.5% sequence identity with a sequence selected from SEQ ID NO:2. In an embodiment, a method of expressing at least one transgene/heterologous coding sequence in a plant comprises growing a plant comprising a gene expression cassette comprising a *Glycine max* egg cell promoter operably linked to at least one transgene. In an embodiment, a method of expressing at least one transgene/heterologous coding sequence in a plant comprises growing a plant comprising a gene expression cassette comprising a *Glycine max* egg cell promoter operably linked to at least one transgene. In an embodiment, a method of expressing at least one transgene/heterologous coding sequence in a plant tissue or plant cell comprises culturing a plant tissue or plant cell comprising a gene expression cassette containing a *Glycine max* egg cell promoter operably linked to at least one transgene. In an embodiment, a method of expressing at least one transgene/heterologous coding sequence in a plant tissue or plant cell comprises culturing a plant tissue or plant cell comprising a gene expression cassette, a *Glycine max* egg cell promoter operably linked to at least one transgene.

In an embodiment, a method of expressing at least one transgene/heterologous coding sequence in a plant comprises growing a plant comprising a *Glycine max* egg cell 3' UTR operably linked to at least one transgene/heterologous coding sequence or a polylinker sequence. In an embodiment the *Glycine max* egg cell 3' UTR consists of a sequence selected from SEQ ID NO:3 or a sequence that has 80%, 85%, 90%, 95% or 99.5% sequence identity with a sequence selected from SEQ ID NO:3. In an embodiment, a method of expressing at least one transgene/heterologous coding sequence in a plant comprising growing a plant comprising a *Glycine max* egg cell 3' UTR operably linked to at least one transgene. In an embodiment, a method of expressing at least one transgene/heterologous coding sequence in a plant tissue or plant cell comprises culturing a plant tissue or plant cell comprising a *Glycine max* egg cell 3' UTR operably linked to at least one transgene.

In an embodiment, a method of expressing at least one transgene/heterologous coding sequence in a plant comprises growing a plant comprising a gene expression cassette comprising a *Glycine max* egg cell 3' UTR operably linked to at least one transgene. In one embodiment the *Glycine max* egg cell 3' UTR consists of a sequence selected from SEQ ID NO:3 or a sequence that has 80%, 85%, 90%, 95% or 99.5% sequence identity with a sequence selected from SEQ ID NO:3. In an embodiment, a method of expressing at least one transgene/heterologous coding sequence in a plant comprises growing a plant comprising a gene expression cassette comprising a *Glycine max* egg cell 3' UTR operably linked to at least one transgene. In an embodiment, a method of expressing at least one transgene/heterologous coding sequence in a plant comprises growing a plant comprising a gene expression cassette comprising a *Glycine max* egg cell 3' UTR operably linked to at least one transgene. In an embodiment, a method of expressing at least one transgene/heterologous coding sequence in a plant tissue or plant cell comprises culturing a plant tissue or plant cell comprising a gene expression cassette containing a *Glycine max* egg cell 3' UTR operably linked to at least one transgene. In an embodiment, a method of expressing at least one transgene/heterologous coding sequence in a plant tissue or plant cell comprises culturing a plant tissue or plant cell comprising a gene expression cassette, a *Glycine max* egg cell 3' UTR operably linked to at least one transgene.

In an embodiment, a method of expressing at least one transgene/heterologous coding sequence in a plant comprises growing a plant comprising a *Glycine max* egg cell terminator operably linked to at least one transgene/heterologous coding sequence or a polylinker sequence. In an embodiment the *Glycine max* egg cell terminator consists of a sequence selected from SEQ ID NO:3 or a sequence that has 80%, 85%, 90%, 95% or 99.5% sequence identity with a sequence selected from SEQ ID NO:3. In an embodiment, a method of expressing at least one transgene/heterologous coding sequence in a plant comprising growing a plant comprising a *Glycine max* egg cell terminator operably linked to at least one transgene. In an embodiment, a method of expressing at least one transgene/heterologous coding sequence in a plant tissue or plant cell comprising culturing a plant tissue or plant cell comprising a *Glycine max* egg cell terminator operably linked to at least one transgene.

In an embodiment, a method of expressing at least one transgene/heterologous coding sequence in a plant comprises growing a plant comprising a gene expression cassette comprising a *Glycine max* egg cell terminator operably linked to at least one transgene. In one embodiment the *Glycine max* egg cell terminator consists of a sequence selected from SEQ ID NO:3 or a sequence that has 80%, 85%, 90%, 95% or 99.5% sequence identity with a sequence selected from SEQ ID NO:3. In an embodiment, a method of expressing at least one transgene/heterologous coding sequence in a plant comprises growing a plant comprising a gene expression cassette comprising a *Glycine max* egg cell terminator operably linked to at least one transgene. In an embodiment, a method of expressing at least one transgene/heterologous coding sequence in a plant comprises growing a plant comprising a gene expression cassette comprising a *Glycine max* egg cell terminator operably linked to at least one transgene. In an embodiment, a method of expressing at least one transgene/heterologous coding sequence in a plant tissue or plant cell comprises culturing a plant tissue or plant cell comprising a gene expression cassette containing a *Glycine max* egg cell terminator operably linked to at least one transgene. In an embodiment, a method of expressing at least one transgene/heterologous coding sequence in a plant tissue or plant cell comprises culturing a plant tissue or plant cell comprising a gene expression cassette, a *Glycine max* egg cell terminator operably linked to at least one transgene.

The following examples are provided to illustrate certain particular features and/or embodiments. The examples should not be construed to limit the disclosure to the particular features or embodiments exemplified.

EXAMPLES

Example 1: Novel Design of a Combination of Optimized Regulatory Elements from Glycine Max Egg Cell Gene The promoter from a *Glycine max* egg cell gene (SEQ ID NO:2) and a 3' UTR from a *Glycine max* egg cell gene (SEQ ID NO:3) was identified from the *Glycine max* genomic DNA (gDNA) sequence. These regulatory element sequences were identified by BLASTing the Phytozome database (Goodstein DM, Shu S, Howson R, Neupane R, Hayes RD, Fazo J, Mitros T, Dirks W, Hellsten U, Putnam N, Rokhsar DS (2012) *Nucleic Acids Res.* 40: D1178-1186) with an *Arabidopsis thaliana* egg cell gene of DD45/EC1.2 (Genbank Acc. No. At2g21740). The resulting hits were analyzed and a single coding sequence was selected for further analysis. For the identification of a novel promoter region, 1 to 3 kb of nucleotides were retrieved upstream of the translational start site (ATG codon) and additional in silico analyses was performed. For the identification of a novel 3' UTR region, 0.5 to 2 kb of nucleotides were retrieved downstream of the stop site and additional in silico analyses was performed. The in silico analyses included the identification of polynucleotide sequences from any other surrounding genes as needed, checking for the presence of repetitive sequences that could result in silencing of gene expression, or the presence of 5' UTRs that may contain non-coding exons and introns. Based on these analyses, the *Glycine max* egg cell promoter sequences were synthesized and moved forward for additional usage to drive expression of a transgened. From the assessment of the contiguous chromosomal sequence that spanned millions of base pairs, a 1,089 bp polynucleotide sequence was identified and isolated for use in expression of heterologous coding sequences as a promoter from SEQ ID NO:1 and is provided as SEQ ID NO:2. This novel polynucleotide sequence was analyzed for use as a regulatory sequence to drive expression of a gene and is provided in the base pairs 1-1,089 of SEQ ID NO:1 and is provided as an SEQ ID NO:3. Likewise, from the assessment of the contiguous chromosomal sequence that spanned millions of base pairs, an 828 bp polynucleotide sequence was identified and isolated for use in terminating of heterologous coding sequences. This novel polynucleotide sequence was analyzed for use as a regulatory sequence to terminate expression of a gene and is provided in the base pairs 1,491-2,318 of SEQ ID NO:1.

Accordingly, SEQ ID NO:1 is provided as:

ACACTACTATAGTGGCCGGTTACTACGTACTAAAATTAGATGAACTTATA

AAATAACAATCAAGTAATGTCAGAACTCTTATGAATAAAAAAATGATTAT

CGTACCTTTAATCAGCTCATTATTTTTTTGGTAAGAATATCAACAGTAA

GCATATGAGTATTTTTTAAGAGAGATATGCTGATTTTGAATTTTGTTTAC

AAAAAAAGCATAAGTAACGTAAAATTGAAAAATTGAATGAAAGTAAATAA

ATGAGAATGTATATATGTACATATGGGAGTATCAAAAGTCTCACCCATGC

TAATGTATATTATTTGTTTTTTTTCTTGATTACATGCAATAAATTATTC

ATTTTTAATTTATATAAATATTATTAAATTTGTTATTATTAATTTTTTGG

GCTGAATAGCAATCAAAGTTTAATACTTTTTTGCGATTATTGCTATATGT

TTTGAAAATTGAGAGAAAATATGATAAATCTGTAATAAAAATAGTAGTAA

GGTAAAAATGTTAACTAACATATAAATGAGAAAAATGAAAAGTTAATAAA

ACATAAACATATAAAATTATAAATTAAATGAATAAATTTTAAAAAATGAC

ATATAACAATCATATATATATATATATATATAGTGGAATATTTTTTTTA

TAAAATAATATATATAACTTGTAGCACGTAATATATAATTAATACGAATT

TGCAGACTCTTTGTTTAGAAATGTATAATTCCCTCATCTATATATATCTT

TTTAATTAAAGAAACTAACGGTCTAATAGATCATTAACAAATCTCCATCA

AATTATAAATTAAAGGAAACAGGAGAGACACTTATTGAATCAATTTACGT

TTAAATTTAATAAAATTAATCTTGATTTCAATCAATGCACAAGATTATTC

ATTTTCGTTATTCATTCATTCCCTTATGTAACCACTGCAAATTAAATTAA

TAATTTTTCACACTCTTCATATCCCCCACACAAACTGTTGCTAAACACAC

TCCCCATACCATTCTCTATATAAACCCCAACCAAGGTGTCACCAGAAATT

AAACCATATTTTCATCTCTTCTTTTCTTCCAAGACTAAAATGCTTCCACT

CACAACCTCTATATCTTTGTTTCTCTTGTGACTATAACTGCATTGGTCTC

ATCAATGGTTGAGTCCAGATCACTCCCTAACGCTTCTTCGAGCCTCACGG

TTCGGTTGAAGCTCGAGGGCGAACCCTCCAACTGTTGGGACTCACTATGG

CAACTCCAAGCATGCAGTGGTGAAATTGTAACGTTTTTTGTCAATGGTGA

GACTTACCTTGGACATGGTTGCTGCCAAGCAATTAGGGTTATTGGACACG

ATTGTTGGCCCAACATTGTTGCGTCTCTAGGATTCACCAATGAAGAGACT

GATGTGTTGGAGGGTTATTGTGATCAAGCTGTTGATTCTCCTTCACCACC

ATCTATAGTAGTTGACTCAAAAGATGACATTGTTCCATAAAGGAAGTTAC

TTTGGTCTTGTTGGTTTCCAATAAATAATTAACTAATAAGGGTCTTGTTT

TGTTTTTTCTTCTCAATTTTGTATGTTGCAACGGATATGGGAAACACATG

CAATATTCTGAATCAATTAATGATATGATATGCAAACAGGGTTGTGTGTT

TTCTATGAATAAAAGGTTGTTGCACATCGGCATTTCGCTTCTTAATTTAT

ATTATATGGCTCTAGTTTTATGTTGAAACTTGAATATGTACAAGTAATTT

GGATAGATAGCGCAGTTAATACTGAATTCATCATTCAATATATAGCAAGG

AAATAAAAATGGAGTTACACTATGGAAGGAGAAGAAAATGATGAAATCTA

GGATATTGCTGCTCTTGATCTTCAACCTTCCAGAGAACCTTGCGCCAGCA

CTCAATTTTGTCAGGGCTTCTTTTAAAAAAAATAATCAAGAATTAAAAAT

-continued

TAAATAAAATATATACACATGGCATGATTAAGAAATTAGCTTGGGGAGAT

TGATCATTAACAGAAAAAAATGGAGTTTATGATCAAATGAAACCACAATA

GGGTGGATGCTGGATGGATTATTTTTACGAGAAAAAAAAAAGCAGATGG

AGGAATAAGAGGTTTGATTCTTGTTCAGTTCCTCCATGAAATATCATATG

TTGATTATATGGATATTTGTTCAGTTGCACATAATGATTGTTCATGTACA

CGAGTTCACTTGCACATGATAATCATTGGTATATATTTTCATGAAACTGT

TAGAATGATCTTGTATTTATTTATTTAATTTTGTTTACTGTTAGCTCTCA

TGGGCACATAGGCGTTAG

Example 2: Vector Construction (pDAB134208)

The pDAB134208 vector was built to incorporate the novel combination of regulatory polynucleotide sequences flanking a transgene. The vector construct pDAB134208 contained a gene expression cassette, in which the RFP transgene was driven by the *Glycine max* egg cell promoter of SEQ ID NO:2, and flanked by *Glycine max* egg cell 3' UTR of SEQ ID NO:3. A sequence listing of this gene expression cassette is provided as SEQ ID NO:5. The vector also contained a selectable marker gene expression cassette that contained the DSM2 transgene (U.S. Patent App. No. 20110107455) driven by the CsVMV promoter (Verdaguer et al., 1996, *Plant Molecular Biology* 31: 1129-1139) and was terminated by the *Agrobacterium* ORF1 3'-UTR (Barker et al, (1983) *Plant Molecular Biology* 2(6): 335-50). A sequence listing of this gene expression cassette is provided as SEQ ID NO:6. This construct was built by synthesizing the newly designed promoter and 3' UTR from a *Glycine max* egg cell gene and cloning the promoter into a GeneArt Seamless Cloning™ (Life Technologies) entry vector using a third party provider. The resulting entry vector was labeled as pDAB129449 contained the *Glycine max* egg cell gene promoter driving the RFP transgene which was used for transformation of *Arabidopsis thaliana* and soybean tissues. Clones of the entry vector, pDAB129449, were obtained and plasmid DNA was isolated and confirmed via restriction enzyme digestions and sequencing. In addition, the pDAB129449 entry vector was integrated into a destination vector pDAB126184 using the Gateway™ cloning system (Life Technologies). Clones of the resulting binary plasmid, pDAB134208, were obtained and plasmid DNA was isolated and confirmed via restriction enzyme digestions and sequencing. The resulting constructs contained a combination of regulatory elements that drive expression of a transgene and terminate expression of a transgene.

Example 3: *Arabidopsis thaliana* Transformation

*Arabidopsis thaliana* Transformation Via *Agrobacterium* Floral Dip

The experimental pDAB134208 construct was transformed into *Arabidopsis* using the floral dip method adapted from Clough and Bent (1998). A validated *Agrobacterium* glycerol stock containing a binary plasmid was used to inoculate a 5 mL pre-culture of YEP broth containing the plasmid's antibiotic selection (spectinomycin (100 mg/L)), and the host's antibiotic selection (kanamycin (50 mg/L) and rifampicin (10 mg/L)). The culture was incubated overnight at 28° C. with aeration. The pre-culture was then bulked up to 250 mL with the same antibiotic selection and incubated again at 28° C. with constant agitation at 225 rpm. The cells were pelleted at approximately 5000×g for 15 minutes at 4° C., and the supernatant discarded. The cell pellet was gently resuspended in 250 mL inoculation medium containing: 10% (w/v) sucrose, 10 µg/L 6-benzylaminopurine, and 0.03% Silwet L-77. Plants at 41 days old (primary inflorescences cut back at 35 days) were inverted and dipped into the medium. The plants (now denoted as T0) were placed on their sides in a transparent covered plastic tub overnight, then set upright in the growth chamber the following day. The plants were grown at 22° C., with a 16-hour light/8-hour dark photoperiod. Four weeks after dipping, the water was cut off and plants were allowed to dry down for a week in preparation for T1 seed harvesting. Selection of Transformed Plants T1 seed was sown on 10.5"×21" germination trays, each receiving a minimum 200 mg aliquot of stratified T1 seed (~10,000 seed) that had previously been suspended in 40 mL of 0.1% agar solution and stored at 4° C. for 2 days to ensure synchronous seed germination (vernalization). Sunshine Mix LP5 soil media was covered with fine vermiculite and sub irrigated with Hoagland's solution until wet, then allowed to gravity drain. Each 40 mL aliquot of stratified seed was sown evenly onto the vermiculite with a pipette and covered with humidity domes for 4-5 days. Domes were removed 1 day prior to initial transformant selection using glufosinate (Liberty). Seven days after planting (DAP) and again at 9 DAP, T1 plants (cotyledon and 2-4 leaf stage, respectively) were sprayed with a 0.2% solution of Liberty herbicide (280 g ai/L glufosinate, Bayer Crop Sciences, Kansas City, MO) at a spray volume of 10 ml/tray (703 L/ha) using a DeVilbiss compressed air spray tip to deliver an effective rate of 42 g ai/ha glufosinate per application. Survivors (putative transformed plants actively growing) were identified 3 days after the final spraying and transplanted individually into 3-inch pots prepared with Sunshine Mix LP5 in the greenhouse 7 days after the final spray selection (16 DAP). The transplants were reared in the greenhouse (22±5° C., 50±30% RH, 14 h light: 10 h dark, minimum 500 µE/m2s1 natural+supplemental light). Molecular analysis (copy number) was completed on the surviving T1 plants to confirm that the herbicide selectable marker gene had integrated into the genome of the plants. Only plants containing one insertion, one copy of the herbicide selectable marker gene were selected for microscopy analysis.

Example 4: Microscopic Analysis of *Glycine Max* Egg Cell-Specific Promoter Expression Patterns in *Arabidopsis* Ovules T1 *Arabidopsis* transgenic plants containing the *Glycine max* egg cell-specific promoter construct pDAB134208 were grown in flats in greenhouse. Wild type plants were grown in the same flats. Flowers from several developmental stages were identified. This included flowers that were newly-opened, flowers with pistils just barely longer than the enclosing petals, and flowers with the pistils approximately twice as long as the petals. Flowers were harvested with #3 forceps into empty scintillation vials and transported back to the microscopy lab. Several drops of water were placed on a slide under a dissecting microscope and #5 TEM forceps were used to open one side of the valve at the replum. Ovules were dissected out of the pistils into the surrounding drop of water and remaining flower parts were removed. The ovules were mounted in PP11 (perfluorodecalin) in a chambered coverglass. Prepared ovules were then imaged by confocal microscopy. The images illustrated an ovule in which the RFP transgene is stably expressed when driven by the *Glycine max* egg cell promoter and transcription terminator containing 3'UTR regulatory elements, it should be noted that the cells/tissue at the micropylar end of the ovules of *Arabidopsis thaliana* robustly express the RFP transgene. Comparatively, the control images illustrated an ovule from the *Arabidopsis thaliana* controls that were not transformed with the *Glycine max* egg cell promoter and transcription terminator containing 3'UTR regulatory elements and do not exhibit expression of the RFP protein. These images describes the detailed structure of *Arabidopsis* ovule (Lawit et al., 2013), which was used as a reference to compare results obtained in this invention Ovules imaged from transgenic line, pDAB134208, showed RFP-expressing cells/tissue at the micropylar end of the ovules. Based on a comparison with the images from the fluorescent micrograph of transgenic ovules visualized with quadruple-labeled expression cassettes at the mature female gametophyte stage demonstrating the cell-specific promoter-fluorescent protein labeling of the antipodals (Zs, tip of the egg cell that is farthest away from the arrow), the central cell (AmCyan), the egg cell (DsRed, arrows), and synergid cells (AcGFP) this RFP-expressing tissue is most highly likely to be the egg cell. No RFP fluorescence was observed near the micropylar end of the ovule obtained from non-transgenic control plant.

The *Glycine max* egg Cell promoter regulatory element of SEQ ID NO:2 and the *Glycine max* egg Cell 3' UTR regulatory element of SEQ ID NO:3, as provided in pDAB134208, resulted in expression of the YFP transgene in *Zea mays* immature embryos. As such, novel *Glycine max* egg cell gene regulatory elements (the *Glycine max* egg cell promoter of SEQ ID NO:2 and the *Glycine max* egg cell 3' UTR of SEQ ID NO:3) were identified and characterized. Disclosed for the first time are novel promoter regulatory elements for use in gene expression constructs.

Example 5: *Agrobacterium*-Mediated Transformation of Genes Operably Linked to the Glycine Max Egg Cell Promoter, the *Glycine max* Egg Cell 5' UTR, the *Glycine max* Egg Cell 3' UTR and/or the *Glycine max* Egg Cell Terminator Soybean may be transformed with genes operably linked to the *Glycine max* egg cell promoter, the *Glycine max* egg cell 5' UTR, the *Glycine max* egg cell 3' UTR and/or the *Glycine max* egg cell terminator by utilizing the same techniques previously described in Example #11 or Example #13 of patent application WO 2007/053482.

Cotton may be transformed with genes operably linked to the *Glycine max* egg cell promoter, the *Glycine max* egg cell 5' UTR, the *Glycine max* egg cell 3' UTR and/or the *Glycine max* egg cell terminator by utilizing the same techniques previously described in Examples #14 of U.S. Pat. No. 7,838,733 or Example #12 of patent application WO 2007/053482 (Wright et al.).

Canola may be transformed with genes operably linked to the *Glycine max* egg cell promoter, the *Glycine max* egg cell 5' UTR, the *Glycine max* egg cell 3' UTR and/or the *Glycine max* egg cell terminator by utilizing the same techniques previously described in Example #26 of U.S. Pat. No. 7,838,733 or Example #22 of patent application WO 2007/053482 (Wright et al.).

Wheat may be transformed with genes operably linked to the *Glycine max* egg cell promoter, the *Glycine max* egg cell 5' UTR, the *Glycine max* egg cell 3' UTR and/or the *Glycine max* egg cell terminator by utilizing the same techniques previously described in Example #23 of patent application WO 2013/116700A1 (Lira et al.).

Rice may be transformed with genes operably linked to the *Glycine max* egg cell promoter, the *Glycine max* egg cell 5' UTR, the *Glycine max* egg cell 3' UTR and/or the *Glycine max* egg cell terminator by utilizing the same techniques previously described in Example #19 of patent application WO 2013/116700A1 (Lira et al.).

Example 6: *Agrobacterium*-Mediated Transformation of Genes Operably Linked to the *Glycine max* Egg Cell Regulatory Elements In light of the subject disclosure, additional crops can be transformed according to embodiments of the subject disclosure using techniques that are known in the art. For *Agrobacterium*-mediated transformation of rye, see, e.g., Popelka JC, Xu J, Altpeter F., "Generation of rye with low transgene copy number after biolistic gene transfer and production of (*Secale cereale* L.) plants instantly marker-free transgenic rye," *Transgenic Res.* 2003 October; 12(5): 587-96.). For *Agrobacterium*-mediated transformation of sorghum, see, e.g., Zhao et al., "*Agrobacterium*-mediated sorghum transformation," *Plant Mol Biol.* 2000 December; 44(6):789-98. For *Agrobacterium*-mediated transformation of barley, see, e.g., Tingay et al., "*Agrobacterium tumefaciens*-mediated barley transformation," *The Plant Journal*, (1997) 11:1369-1376. For *Agrobacterium*-mediated transformation of wheat, see, e.g., Cheng et al., "Genetic Transformation of Wheat Mediated by *Agrobacterium tumefaciens*," *Plant Physiol.* 1997 November; 115(3):971-980. For *Agrobacterium*-mediated transformation of rice, see, e.g., Hiei et al., "Transformation of rice mediated by *Agrobacterium tumefaciens*," *Plant Mol. Biol.* 1997 September; 35(1-2):205-18.

The Latin names for these and other plants are given below. It should be clear that other (non-*Agrobacterium*) transformation techniques can be used to transform genes operably linked to *Glycine max* egg cell promoter, the *Glycine max* egg cell 5' UTR, the *Glycine max* egg cell 3' UTR and/or the *Glycine max* egg cell terminator, for example, into these and other plants. Examples include, but are not limited to; Maize (*Zea mays*), Wheat (*Triticum* spp.), Rice (*Oryza* spp. and Zizania spp.), Barley (*Hordeum* spp.), Cotton (Abroma augusta and *Gossypium* spp.), Soybean (*Glycine max*), Sugar and table beets (Beta spp.), Sugar cane (*Arenga pinnata*), Tomato (*Lycopersicon esculentum* and other spp., Physalis ixocarpa, *Solanum incanum* and other spp., and Cyphomandra betacea), Potato (*Solanum tuberosum*), Sweet potato (*Ipomoea batatas*), Rye (*Secale* spp.), Peppers (*Capsicum annuum, chinense*, andfrutescens), Lettuce (*Lactuca sativa, perennis*, and *pulchella*), Cabbage (*Brassica* spp.), Celery (*Apium graveolens*), Eggplant (*Solanum melongena*), Peanut (*Arachis hypogea*), Sorghum (Sorghum spp.), Alfalfa (*Medicago sativa*), Carrot (*Daucus carota*), Beans (*Phaseolus* spp. and other genera), Oats (*Avena sativa* and *strigosa*), Peas (*Pisum, Vigna*, and Tetragonolobus spp.), Sunflower (*Helianthus annuus*), Squash (*Cucurbita* spp.), Cucumber (*Cucumis sativa*), Tobacco (*Nicotiana* spp.), Arabidopsis (*Arabidopsis thaliana*), Turfgrass (*Lolium, Agrostis, Poa, Cynodon*, and other genera), Clover (*Trifolium*), Vetch (*Vicia*). Transformation of such plants, with genes operably linked to the *Glycine max* egg cell promoter, the *Glycine max* egg cell 5' UTR, the *Glycine max* egg cell 3' UTR and/or the *Glycine max* egg cell terminator, for example, is contemplated in embodiments of the subject disclosure.

Use of the *Glycine max* egg cell promoter, the *Glycine max* egg cell 5' UTR, the *Glycine max* egg cell 3' UTR and/or the *Glycine max* egg cell terminator to drive operably linked genes can be deployed in many deciduous and evergreen timber species. Such applications are also within the scope of embodiments of this disclosure. These species include, but are not limited to; alder (*Alnus* spp.), ash (*Fraxinus* spp.), aspen and poplar species (*Populus* spp.), beech (*Fagus* spp.), birch (*Betula* spp.), cherry (*Prunus* spp.), eucalyptus (*Eucalyptus* spp.), hickory (*Carya* spp.), maple (Acer spp.), oak (*Quercus* spp.), and pine (*Pinus* spp.).

Use of *Glycine max* egg cell promoter, the *Glycine max* egg cell 5' UTR, the *Glycine max* egg cell 3' UTR and/or the *Glycine max* egg cell terminator to drive operably linked genes can be deployed in ornamental and fruit-bearing species. Such applications are also within the scope of embodiments of this disclosure. Examples include, but are not limited to; rose (Rosa spp.), burning bush (*Euonymus* spp.), petunia (*Petunia* spp.), begonia (*Begonia* spp.), *rhododendron* (*Rhododendron* spp.), crabapple or apple (Malus spp.), pear (*Pyrus* spp.), peach (*Prunus* spp.), and marigolds (*Tagetes* spp.).

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A nucleic acid vector comprising a 3' UTR operably linked to: a) a heterologous polylinker sequence; or b) a non-*Glycine max* egg cell polynucleotide sequence, wherein said 3' UTR comprises a polynucleotide sequence that has at least 97% sequence identity with SEQ ID NO:3.

2. The nucleic acid vector of claim 1, wherein said 3' UTR is 739 bp in length.

3. The nucleic acid vector of claim 1, wherein said 3' UTR consists of a polynucleotide sequence that has at least 97% sequence identity with SEQ ID NO:3.

4. The nucleic acid vector of claim 1, further comprising a sequence encoding a selectable maker.

5. The nucleic acid vector of claim 1, wherein said non-*Glycine max* egg cell polynucleotide sequence is a transgene.

6. The nucleic acid vector of claim 1, wherein the transgene encodes a selectable marker or a gene product conferring insecticidal resistance, herbicide tolerance, expression of an RNAi, nitrogen use efficiency, water use efficiency, or nutritional quality.

7. The nucleic acid vector of claim 1, further comprising a promoter polynucleotide sequence of SEQ ID NO:2, wherein the promoter sequence is operably linked to said polylinker or said non-*Glycine max* egg cd polynucleotide sequence.

8. The nucleic acid vector of claim 7, further comprising an intron sequence.

9. The nucleic acid vector of claim 7, wherein said promoter has tissue preferred specific expression.

* * * * *

SEQUENCE LISTING

```
<160> NUMBER OF SEQ ID NOS: 6

<210> SEQ ID NO 1
<211> LENGTH: 2318
<212> TYPE: DNA
<213> ORGANISM: Glycine Max

<400> SEQUENCE: 1
acactactat agtggccggt tactacgtac taaaattaga tgaacttata aaataacaat      60
caagtaatgt cagaactctt atgaataaaa aaatgattat cgtaccttta atcagctcat     120 tattttttt ggtaagaata tcaacagtaa gcatatgagt atttttttaag agagatatgc     180 tgattttgaa ttttgtttac aaaaaaagca taagtaacgt aaaattgaaa aattgaatga     240
```

| | | | | |
|---|---|---|---|---|
| aagtaaataa | atgagaatgt | atatatgtac | atatgggagt | atcaaaagtc tcacccatgc | 300 |
| taatgtatat | tatttgtttt | ttttcttga | ttacatgcaa | taaattattc atttttaatt | 360 |
| tatataaata | ttattaaatt | tgttattatt | aattttttgg | gctgaatagc aatcaaagtt | 420 |
| taatactttt | ttgcgattat | tgctatatgt | tttgaaaatt | gagagaaaat atgataaatc | 480 |
| tgtaataaaa | atagtagtaa | ggtaaaaatg | ttaactaaca | tataaatgag aaaaatgaaa | 540 |
| agttaataaa | acataaacat | ataaaattat | aaattaaatg | aataaatttt aaaaaatgac | 600 |
| ataacaat | catatatata | tatatatata | tagtggaata | ttttttttta taaaataata | 660 |
| tataactt | gtagcacgta | atatataatt | aatacgaatt | tgcagactct ttgtttagaa | 720 |
| atgtataatt | ccctcatcta | tatatatctt | tttaattaaa | gaaactaacg gtctaataga | 780 |
| tcattaacaa | atctccatca | aattataaat | taaaggaaac | aggagagaca cttattgaat | 840 |
| caatttacgt | ttaaatttaa | taaaattaat | cttgatttca | atcaatgcac aagattattc | 900 |
| attttcgtta | ttcattcatt | cccttatgta | accactgcaa | attaaattaa taattttca | 960 |
| cactcttcat | atccccaca | caaactgttg | ctaaacacac | tccccatacc attctctata | 1020 |
| taaaccccaa | ccaaggtgtc | accagaaatt | aaaccatatt | ttcatctctt ctttctttcc | 1080 |
| aagactaaaa | tgcttccact | cacaacctct | atatctttgt | ttctcttgtg actataactg | 1140 |
| cattggtctc | atcaatggtt | gagtccagat | cactccctaa | cgcttcttcg agcctcacgg | 1200 |
| ttcggttgaa | gctcgagggc | gaaccctcca | actgttggga | ctcactatgg caactccaag | 1260 |
| catgcagtgg | tgaaattgta | acgtttttg | tcaatggtga | gacttacctt ggacatggtt | 1320 |
| gctgccaagc | aattagggtt | attggacacg | attgttggcc | caacattgtt gcgtctctag | 1380 |
| gattcaccaa | tgaagagact | gatgtgttgg | agggttattg | tgatcaagct gttgattctc | 1440 |
| cttcaccacc | atctatagta | gttgactcaa | aagatgacat | tgttccataa aggaagttac | 1500 |
| tttggtcttg | ttggttcca | ataaataatt | aactaataag | ggtcttgttt tgttttttct | 1560 |
| tctcaattt | gtatgttgca | acggatatgg | gaaacacatg | caatattctg aatcaattaa | 1620 |
| tgatatgata | tgcaaacagg | gttgtgtgtt | ttctatgaat | aaaaggttgt tgcacatcgg | 1680 |
| catttcgctt | cttaatttat | attatatggc | tctagtttta | tgttgaaact tgaatatgta | 1740 |
| caagtaattt | ggatagatag | cgcagttaat | actgaattca | tcattcaata tatagcaagg | 1800 |
| aaataaaaat | ggagttacac | tatggaagga | gaagaaaatg | atgaaatcta ggatattgct | 1860 |
| gctcttgatc | ttcaaccttc | cagagaacct | tgcgccagca | ctcaattttg tcagggcttc | 1920 |
| ttttaaaaaa | aataatcaag | aattaaaaat | taaataaaat | atatacacat ggcatgatta | 1980 |
| agaaattagc | ttggggagat | tgatcattaa | cagaaaaaaa | tggagtttat gatcaaatga | 2040 |
| aaccacaata | gggtggatgc | tggatggatt | atttttacga | gaaaaaaaaa aagcagatgg | 2100 |
| aggaataaga | ggtttgattc | ttgttcagtt | cctccatgaa | atatcatatg ttgattatat | 2160 |
| ggatatttgt | tcagttgcac | ataatgattg | ttcatgtaca | cgagttcact tgcacatgat | 2220 |
| aatcattggt | atatattttc | atgaaactgt | tagaatgatc | ttgtatttat ttatttaatt | 2280 |
| ttgtttactg | ttagctctca | tgggcacata | ggcgttag | | 2318 |

<210> SEQ ID NO 2
<211> LENGTH: 1089
<212> TYPE: DNA
<213> ORGANISM: Glycine max

<400> SEQUENCE: 2

-continued

```
acactactat agtggccggt tactacgtac taaaattaga tgaacttata aaataacaat      60
caagtaatgt cagaactctt atgaataaaa aaatgattat cgtacccttta atcagctcat    120 tattttttt ggtaagaata tcaacagtaa gcatatgagt atttttttaag agagatatgc    180 tgattttgaa ttttgtttac aaaaaaagca taagtaacgt aaaattgaaa aattgaatga    240
aagtaaataa atgagaatgt atatatgtac atatgggagt atcaaaagtc tcacccatgc    300
taatgtatat tatttgtttt tttttcttga ttacatgcaa taaattattc attttttaatt    360 tatataaata ttattaaatt tgttattatt aattttttgg gctgaatagc aatcaaagtt    420
taatactttt ttgcgattat tgctatatgt tttgaaaatt gagagaaaat atgataaatc    480
tgtaataaaa atagtagtaa ggtaaaaatg ttaactaaca tataaatgag aaaaatgaaa    540
agttaataaa acataaacat ataaaattat aaattaaatg aataaatttt aaaaaatgac    600
atataacaat catatatata tatatatata tagtggaata ttttttttta taaaataata    660
tatataactt gtagcacgta atatataatt aatacgaatt tgcagactct ttgtttagaa    720
atgtataatt ccctcatcta tatatatctt tttaattaaa gaaactaacg gtctaataga    780
tcattaacaa atctccatca aattataaat taaaggaaac aggagagaca cttattgaat    840
caatttacgt ttaaatttaa taaaattaat cttgatttca atcaatgcac aagattattc    900
attttcgtta ttcattcatt cccttatgta accactgcaa attaaattaa taatttttca    960
cactcttcat atcccccaca caaactgttg ctaaacacac tccccatacc attctctata   1020
taaaccccaa ccaaggtgtc accagaaatt aaaccatatt ttcatctctt cttttcttcc   1080
aagactaaa                                                           1089

<210> SEQ ID NO 3
<211> LENGTH: 828
<212> TYPE: DNA
<213> ORGANISM: Glycine max

<400> SEQUENCE: 3
aggaagttac tttggtcttg ttggtttcca ataaataatt aactaataag ggtcttgttt      60
tgttttttct tctcaattt gtatgttgca acggatatgg gaaacacatg caatattctg    120
aatcaattaa tgatatgata tgcaaacagg gttgtgtgtt ttctatgaat aaaaggttgt    180
tgcacatcgg catttcgctt cttaatttat attatatggc tctagtttta tgttgaaact    240
tgaatatgta caagtaattt ggatagatag cgcagttaat actgaattca tcattcaata    300
tatagcaagg aaataaaaat ggagttacac tatggaagga gaagaaaatg atgaaatcta    360
ggatattgct gctcttgatc ttcaaccttc cagagaacct tgcgccagca ctcaattttg    420
tcagggcttc ttttaaaaaa aataatcaag aattaaaaat taaataaaat atatacacat    480
ggcatgatta agaaattagc ttggggagat tgatcattaa cagaaaaaaa tggagtttat    540
gatcaaatga aaccacaata gggtggatgc tggatggatt atttttacga gaaaaaaaaa    600
aagcagatgg aggaataaga ggtttgattc ttgttcagtt cctccatgaa atatcatatg    660
ttgattatat ggatatttgt tcagttgcac ataatgattg ttcatgtaca cgagttcact    720
tgcacatgat aatcattggt atatattttc atgaaactgt tagaatgatc ttgtatttat    780
ttatttaatt ttgtttactg ttagctctca tgggcacata ggcgttag                 828

<210> SEQ ID NO 4
<211> LENGTH: 401
<212> TYPE: DNA
<213> ORGANISM: Glycine max
```

<400> SEQUENCE: 4

```
atgcttccac tcacaacctc tatatctttg tttctcttgt gactataact gcattggtct      60
catcaatggt tgagtccaga tcactcccta acgcttcttc gagcctcacg gttcggttga     120
agctcgaggg cgaaccctcc aactgttggg actcactatg caactccaa gcatgcagtg     180
gtgaaattgt aacgttttt gtcaatggtg agacttacct tggacatggt tgctgccaag     240
caattagggt tattggacac gattgttggc ccaacattgt tgcgtctcta ggattccaca     300
atgaagagac tgatgtgttg gagggttatt gtgatcaagc tgttgattct ccttcaccac     360
catctatagt agttgactca aaagatgaca ttgttccata a                         401
```

<210> SEQ ID NO 5
<211> LENGTH: 2660
<212> TYPE: DNA
<213> ORGANISM: Artificial Sequence
<220> FEATURE:
<223> OTHER INFORMATION: Gene expression cassette containing the Glycine max egg cell promoter :: RFP :: Glycine max 3' UTR

<400> SEQUENCE: 5

```
acactactat agtggccggt tactacgtac taaaattaga tgaacttata aataacaat       60
caagtaatgt cagaactctt atgaataaaa aaatgattat cgtacccttta atcagctcat    120
tatttttttt ggtaagaata tcaacagtaa gcatatgagt atttttaag agagatatgc     180
tgattttgaa ttttgtttac aaaaaaagca taagtaacgt aaaattgaaa aattgaatga     240
aagtaaataa atgagaatgt atatatgtac atatgggagt atcaaaagtc tcacccatgc     300
taatgtatat tatttgtttt ttttttcttga ttacatgcaa taattattc attttttaatt   360
tatataaata ttattaaatt tgttattatt aattttttgg gctgaatagc aatcaaagtt     420
taatactttt ttgcgattat tgctatatgt tttgaaaatt gagagaaaat atgataaatc     480
tgtaataaaa atagtagtaa ggtaaaaatg ttaactaaca tataaatgag aaaaatgaaa     540
agttaataaa acataaacat ataaaattat aaattaaatg aataaattt aaaaaatgac     600
atataacaat catatatata tatatatata tagtggaata ttttttttta taaaataata     660
tataactt gtagcacgta atatataatt aatacgaatt tgcagactct tgtttagaa        720
atgtataatt ccctcatcta tatatatctt tttaattaaa gaaactaacg gtctaataga    780
tcattaacaa atctccatca aattataaat taaaggaaac aggagagaca cttattgaat     840
caatttacgt ttaaatttaa taaaattaat cttgatttca atcaatgcac aagattattc     900
attttcgtta ttcattcatt ccctatgta accactgcaa attaaattaa tattttttca     960
cactcttcat atccccaca caaactgttg ctaaacacac tccccatacc attctctata    1020
taaaccccaa ccaaggtgtc accagaaatt aaaccatatt ttcatctctt cttttcttcc   1080
aagactaaat gactagctga cgcggcagcc atgtctgaac tcatcaaaga gaacatgcac   1140
atgaagttgt acatggaagg cacagtcaac aatcatcact tcaagtgcac atctgaggga   1200
gaaggcaaac cctatgaagg cactcagacc atgaagatca agttgtgga aggtggacca     1260
cttcccttg cattcgacat tcttgccaca agtttcatgt atgggtcaaa ggcattcatc    1320
aaccacaccc aagggatacc agactttttc aaacaaagct ttcctgaagg cttcacatgg    1380
gagaggataa caacctatga ggatggtgga gttctgactg ccactcaaga tacctctttc    1440
cagaatggct gcattatcta caatgtcaag atcaatggtt gaactttcc gtccaatggt     1500
cctgtcatgc aaaagaaaac aagagggtgg gaagccaaca ctgagatgtt gtacccagct    1560
```

```
gatggtggac tgagaggaca ttcacaaatg gctctgaaac tcgttggtgg aggctacttg    1620
cattgtagtt tcaagactac ctatcgatcc aagaaaccag ccaagaatct caagatgcct    1680
gggtttcact tgtggatca tcgtttggag aggattaagg aggctgacaa agaaacctat     1740
gtggagcagc atgagatggc agttgctaag tactgtgatc ttccgagcaa acttggacac    1800
cgatgagtag ttagcttaat cacctagagc tcaggaagtt actttggtct tgttggtttc    1860
caataaataa ttaactaata agggtcttgt tttgttttt cttctcaatt ttgtatgttg     1920
caacggatat gggaaacaca tgcaatattc tgaatcaatt aatgatatga tatgcaaaca    1980
gggttgtgtg ttttctatga ataaaaggtt gttgcacatc ggcatttcgc ttcttaattt    2040
atattatatg gctctagttt tatgttgaaa cttgaatatg tacaagtaat ttggatagat    2100
agcgcagtta atactgaatt catcattcaa tatatagcaa ggaaataaaa atggagttac    2160
actatggaag gagaagaaaa tgatgaaatc taggatattg ctgctcttga tcttcaacct    2220
tccagagaac cttgcgccag cactcaattt tgtcagggct tcttttaaaa aaataatca    2280 agaattaaaa attaaataaa atatatacac atggcatgat taagaaatta gcttggggag    2340
attgatcatt aacagaaaaa aatggagttt atgatcaaat gaaaccacaa tagggtggat    2400
gctggatgga ttattttac gagaaaaaaa aaaagcagat ggaggaataa gaggtttgat     2460
tcttgttcag ttcctccatg aaatatcata tgttgattat atggatattt gttcagttgc    2520
acataatgat tgttcatgta cacgagttca cttgcacatg ataatcattg gtatatattt    2580
tcatgaaact gttagaatga tcttgtattt atttatttaa ttttgtttac tgttagctct    2640
catgggcaca taggcgttag                                                 2660

<210> SEQ ID NO 6
<211> LENGTH: 1771
<212> TYPE: DNA
<213> ORGANISM: Artificial Sequence
<220> FEATURE:
<223> OTHER INFORMATION: Gene expression cassette containing CsVMV
      promoter :: DSM-2 :: Atu ORF1 3' UTR

<400> SEQUENCE: 6
ccagaaggta attatccaag atgtagcatc aagaatccaa tgtttacggg aaaaactatg      60
gaagtattat gtaagctcag caagaagcag atcaatatgc ggcacatatg caacctatgt     120
tcaaaaatga agaatgtaca gatacaagat cctatactgc cagaatacga agaagaatac     180
gtagaaattg aaaagaaga accaggcgaa gaaaagaatc ttgaagacgt aagcactgac      240
gacaacaatg aaaagaagaa gataaggtcg gtgattgtga agagacata gaggacacat      300 gtaaggtgga aaatgtaagg gcggaaagta accttatcac aaaggaatct tatccccac      360 tacttatcct tttatatttt tccgtgtcat ttttgccctt gagttttcct atataaggaa     420
ccaagttcgg catttgtgaa aacaagaaaa aatttggtgt aagctatttt ctttgaagta     480
ctgaggatac aacttcagag aaatttgtaa gtttgtagat ctccatgcct ggaactgctg     540
aggtccaagt tcgccctgga gtcgaagagg acctcaaacc actcaccgat ctctacaacc    600
actacgttcg tgagactcca ataacctttg acactgagcc attcactcca gaagagcgta    660
ggccttggct tttgagccac ccagaagatg gcccttatag gttgagggtt gccaccgatg    720
cagagtccca agaaatcctt ggctacgcca cctcaagccc ctacagagcc aagccagcat    780
acgcaacctc tgtggaaaca acagtctatg ttgcccctgg tgctggtgga cgtggaattg    840
ggtctctcct ttatgcctcc ctctttgacg cccttgctgc cgaggacctt cacagagctt    900
```

```
atgctggcat cgctcagccc aatgaggcat cagcacgctt gcatgctagg tttggtttca        960
gacatgtggg cacttaccgc gaagtgggga ggaagtttgg tcgttactgg gatgtggctt       1020
ggtatgagag acccttgtga gtagttagct taatcaccta gagctcagat cggcggcaat       1080
agcttcttag cgccatcccg ggttgatcct atctgtgttg aaatagttgc ggtgggcaag       1140
gctctctttc agaaagacag gcggccaaag gaacccaagg tgaggtgggc tatggctctc       1200
agttccttgt ggaagcgctt ggtctaaggt gcagaggtgt tagcggggat gaagcaaaag       1260
tgtccgattg taacaagata tgttgatcct acgtaaggat attaaagtat gtattcatca       1320
ctaatataat cagtgtattc caatatgtac tacgatttcc aatgtcttta ttgtcgccgt       1380
atgcaatcgg cgtcacaaaa taatccccgg tgactttctt ttaatccagg atgaaataat       1440
atgttattat aattttttgcg atttggtccg ttataggaat tgaagtgtgc ttgcggtcgc       1500
caccactccc atttcataat tttacatgta tttgaaaaat aaaaatttat ggtattcaat       1560
ttaaacacgt atacttgtaa agaatgatat cttgaaagaa atatagttta aatatttatt       1620
gataaaataa caagtcaggt attatagtcc aagcaaaaac ataaatttat tgatgcaagt       1680
ttaaattcag aaatatttca ataactgatt atatcagctg gtacattgcc gtagatgaaa       1740
gactgagtgc gatattatgg tgtaatacat a                                     1771
```